US012673115B2

(12) United States Patent
Stephanopoulos et al.

(10) Patent No.: US 12,673,115 B2
(45) Date of Patent: Jul. 7, 2026

(54) NUCLEIC ACID-PEPTIDE-NUCLEIC ACID CONJUGATE MOLECULES AND METHODS OF MAKING THE SAME

(71) Applicants: Nicholas Stephanopoulos, Scottsdale, AZ (US); Tara MacCulloch, Scottsdale, AZ (US)

(72) Inventors: Nicholas Stephanopoulos, Scottsdale, AZ (US); Tara MacCulloch, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 943 days.

(21) Appl. No.: 17/818,856

(22) Filed: Aug. 10, 2022

(65) Prior Publication Data

US 2023/0053360 A1 Feb. 23, 2023

Related U.S. Application Data

(60) Provisional application No. 63/231,974, filed on Aug. 11, 2021.

(51) Int. Cl.
| | |
|---|---|
| *C12N 15/113* | (2010.01) |
| *A61K 47/54* | (2017.01) |
| *A61K 47/64* | (2017.01) |
| *A61K 47/69* | (2017.01) |

(52) U.S. Cl.
CPC ........ *A61K 47/6925* (2017.08); *A61K 47/549* (2017.08); *A61K 47/64* (2017.08); *C12N 15/113* (2013.01); *C12N 2310/18* (2013.01); *C12N 2310/3513* (2013.01)

(58) Field of Classification Search
CPC .............. C12N 15/113; C12N 2310/11; C12N 2310/122; C12N 2310/3513
USPC ...................................................... 536/25.3
See application file for complete search history.

(56) References Cited

FOREIGN PATENT DOCUMENTS

WO WO-2021113851 A2 * 6/2021 ......... A61K 47/6455

OTHER PUBLICATIONS

Hayashi et al., Biomacromolecules, 2019, vo.. 20, pp. 1246-1253. (Year: 2019).*

Rogers et al.,"Nucleic Acids Research," 2004, 32, 6595-6604.
Roglin et al.,"Chembiochem : a European journal of chemical biology," 2009, 10, 758-765.
Rosen et al., "Nature chemistry," 2014, 6, 804-809.
Sa-Ardyen et al., "Biophysical Journal," 2003, 84, 3829-3837.
Samanen et al., "Journal of medicinal chemistry," 1991, 34, 3114-3125.
Seeman, "Annual Review of Biophysics and Biomolecular Structure," 1998, 27, 225-248.
Shadidi et al., "Drug Resistance Updates," 2003, 6, 363-371.
Sprengel et al., "Nature communications," 2017, 8, 14472-14472.
Spruijt et al., "Nature Nanotechnology," 2018, 13, 739-+.
Stephanopoulos, N., "Hybrid Nanostructures from the Self-Assembly of Proteins and DNA", Chem, 6, pp. 364-405, 2020.
Stephanopoulos et al., "Nano Letters," 2015, 15, 603-609.
Taskova et al., "Chembiochem", 2017, 18, 1671-1682.
Thurley et al., "Journal of the American Chemical Society," 2007, 129, 12693-12695.
Van Agthoven et al., "Nature structural & molecular biology," 2014, 21, 383-388.
White et al.,"Nature chemistry," 2011, 3, 509-524.
Williams et al.,"Angewandte Chemie-International Edition," 2007, 46, 3051-3054.
Winfree et al., "Nature," 1998, 394, 539-544.
Xia et al., "Biochemistry," 2016, 55, 1326-1331.
Zhang et al., "Nature Chemistry," 2011, 3, 103-113.
Zubin et al., "Febs Letters," 1999, 456, 59-62.
Abes et al., "Journal of Controlled Release," 2006, 116, 304-313.
Abes et al., "Biochemical Society Transactions," 2007, 35, 53-55.
Assa-Munt et al., "Biochemistry (Easton)," 2001, 40, 2373-2378.
Astakhova et al., "Molecular pharmaceutics," 2018, 15, 2892-2899.
Aumailley et al., "FEBS letters," 1991, 291, 50-54.
Badeau et al., "Nature chemistry," 2018, 10, 251-258.
Bruick et al., "Chemistry & Biology," 1996, 3, 49-56.

(Continued)

*Primary Examiner* — Traviss C McIntosh, III
(74) *Attorney, Agent, or Firm* — Quarles & Brady LLP

(57) ABSTRACT

The present disclosure relates to nucleic acid-peptide-nucleic acid conjugate molecules and to methods for synthesizing nucleic acid-peptide-nucleic acid conjugate molecules. In some embodiments, a method for synthesizing a nucleic acid-peptide-nucleic acid conjugate molecule using proximity-enhanced synthesis includes covalently linking a peptide with a first nucleic acid strand via a first reaction, hybridizing the first nucleic acid strand with a second nucleic acid strand to bring the second nucleic acid strand in proximity to the peptide, and covalently linking the peptide with the second nucleic acid strand via a second reaction to provide the nucleic acid-peptide-nucleic acid conjugate molecule. In some embodiments, the peptide of the nucleic acid-peptide-nucleic acid conjugate molecule is a substrate for cleavage by an enzyme, such as matrix metalloproteinase-8 (MMP-8). Exemplary applications of the nucleic acid-peptide-nucleic acid conjugate molecule for drug delivery, molecular assembly of hybrid structures, and constraining the peptide to a biologically active conformation are also disclosed.

13 Claims, 9 Drawing Sheets

Specification includes a Sequence Listing.

(56) References Cited

OTHER PUBLICATIONS

Buchberger et al., "Journal of the American Chemical Society," 2020, 142, 1406-1416.
Buchberger et al., "Chembiochem : a European journal of chemical biology," 2021, 22, 1755-1760.
Chau et al. "Bioconjugate Chemistry," 2004, 15, 931-941.
Chau et al., "Biomaterials," 2008, 29, 1713-1719.
Chotera et al., "Chemistry—a European Journal," 2018, 24, 10128-10135.
Cordier et al., "Plos One," 2014, 9.
Daly et al., "Bioconjugate chemistry," 2019, 30, 1864-1869.
Diezmann et al., Organic & biomolecular chemistry, 2015, 13, 8008-8015.
Douglas et al.,, "Science," 2012, 335, 831-834.
Eberhard et al., Angewandte Chemie-International Edition, 2011, 50, 4146-4150.
Erben et al.,"Angewandte Chemie-International Edition," 2011, 50, 2828-2832.
Finke et al., "Angewandte Chemie-International Edition," 2016, 55, 10136-10140.
Fischbach et al., "Angewandte Chemie (International ed.)," 2014, 53, 11955-11959.
Freeman et al., "Science (American Association for the Advancement of Science)," 2018, 362, 808-813.
Freeman et al.,"Nature Communications," 2017, 8.
Fu et al.,"Biochemistry," 1993, 32, 3211-3220.
Ghosh et al., "Journal of the American Chemical Society," 2012, 134, 13208-13211.
Gooding et al., "European Journal of Pharmaceutics and Biopharmaceutics," 2016, 107, 321-340.
Gour et al., "Chemical Communications," 2012, 48, 5440-5442.
Guo et al., "Journal of the American Chemical Society," 2015, 137, 11191-11196.

Gutierrez-Fernandez et al., "Cancer research (Chicago, III.)," 2008, 68, 2755-2763.
Han et al.,"Science (American Association for the Advancement of Science)," 2017, 358, eaao2648.
Hayashi et al., "Biomacromolecules," 2019, 20, 1246-1253.
Juliano et al., "Nucleic Acids Research", 2008, 36, 4158-4171.
Kang et al., "Journal of the American Chemical Society," 2014, 136, 3687-3694.
Kapp et al., "Scientific reports," 2017, 7, 39805-39805.
Krammer et al., "Matrix biology," 2002, 21, 139-147.
Kye and Y. B. Lim, "Angewandte Chemie-International Edition," 2016, 55, 12003-12007.
Leahy et al.,"Cell (Cambridge)," 1996, 84, 155-164.
Lee et al., "Nature Nanotechnology," 2012, 7, 389-393.
Li et al., "Angewandte Chemie-International Edition," 2015, 54, 3957-3961.
Li et al., "Nature nanotechnology," 2018, 13, 723-729.
Li et al., "Small," 2015, 11, 1138-1143.
Li et al.,"Journal of the American Chemical Society," 1996, 118, 6131-6140.
MacCulloch et al., "Organic & Biomolecular Chemistry," 2019, 17, 1668-1682.
Machida et al.,"Angewandte Chemie (International ed.)," 2016, 55, 8595-8598.
Marczynke et al.,"Bioconjugate chemistry," 2017, 28, 2384-2392.
Middel et al.,"Chembiochem," 2017, 18, 2328-2332.
Niu et al.,"Nature Chemistry," 2013, 5, 282-292.
Oh et al., "Chemical communications (Cambridge, England)," 2007, 4869-4871.
Patel et al.,"Biomacromolecules," 2012, 13, 2546-2553.
Patutina et al., "Biomaterials," 2017, 122, 163-178.
Pfaff et al., "The Journal of biological chemistry," 1994, 269, 20233-20238.
Roglin, L., M. R. Ahmadian and O. Seitz, "Angewandte Chemie (International ed.)," 2007, 46, 2704-2707.

* cited by examiner

FIG. 1

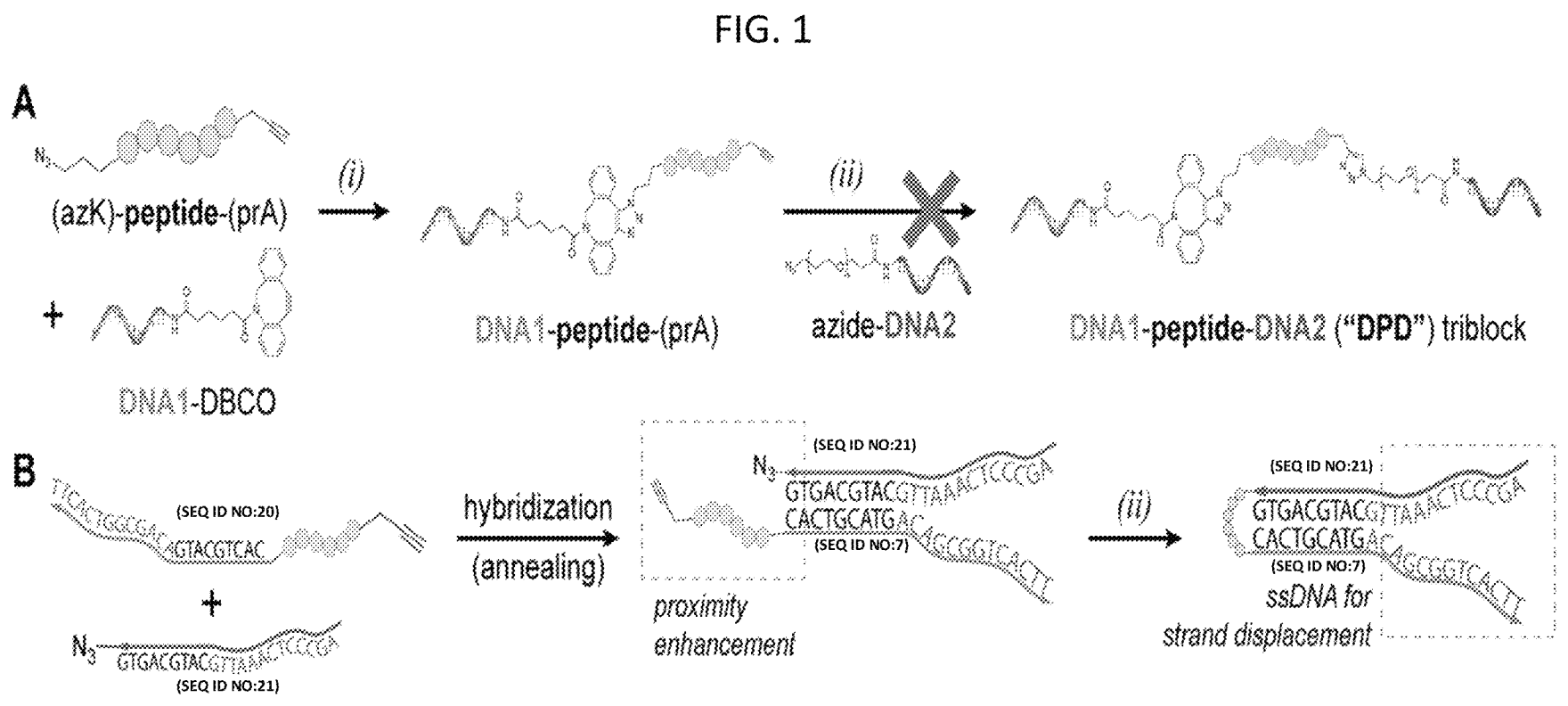

A (azK)-peptide-(prA)

+

DNA1-DBCO

DNA1-peptide-(prA)

azide-DNA2

DNA1-peptide-DNA2 ("DPD") triblock

B (SEQ ID NO:20)

(SEQ ID NO:21)

hybridization (annealing)

proximity enhancement (SEQ ID NO:21)

(SEQ ID NO:7)

(SEQ ID NO:21)

(SEQ ID NO:7)

ssDNA for strand displacement

A

MMP<sub>pep</sub> = (prA)GGPQGIWGQG(azK)
(SEQ ID NO:2)

B

RGDS<sub>pep</sub> = (prA)GRGDSG(azK)
(SEQ ID NO:3)

C

DBCO-sulfo-NHS

D

NHS-(PEG)<sub>4</sub>-azide

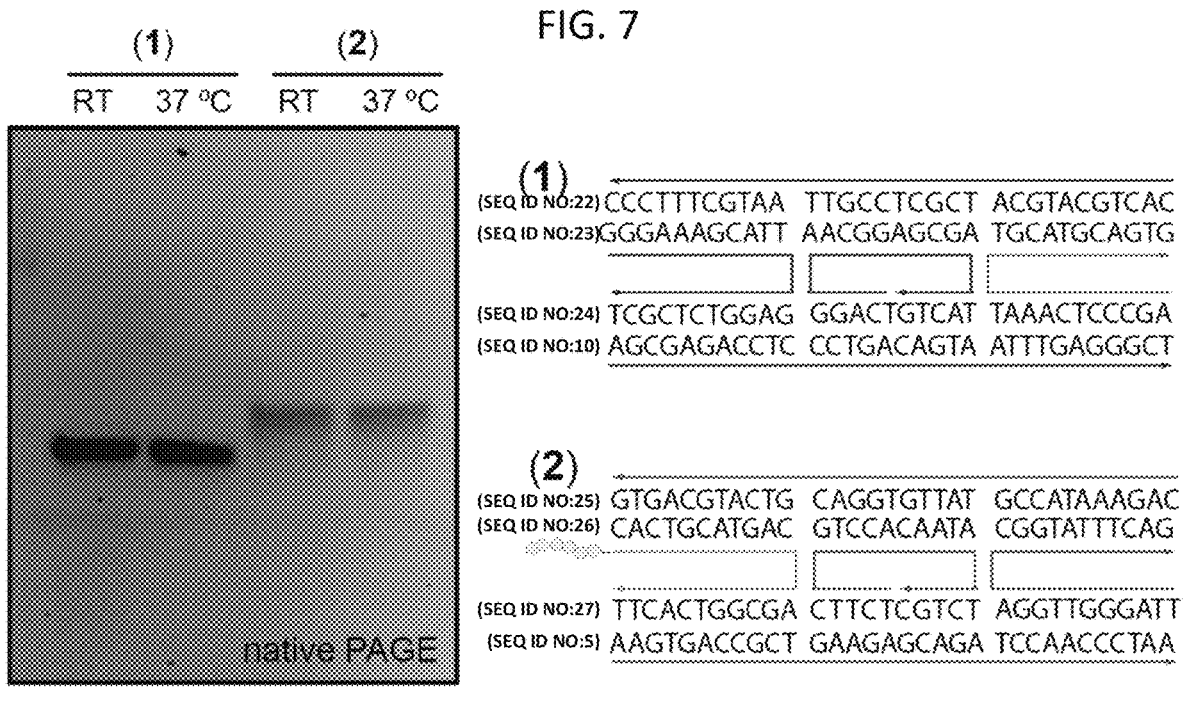

(1)
(SEQ ID NO:22) CCCTTTCGTAA TTGCCTCGCT ACGTACGTCAC
(SEQ ID NO:23) GGGAAAGCATT AACGGAGCGA TGCATGCAGTG (SEQ ID NO:24) TCGCTCTGGAG GGACTGTCAT TAAACTCCCGA
(SEQ ID NO:10) AGCGAGACCTC CCTGACAGTA ATTTGAGGGCT (2)
(SEQ ID NO:25) GTGACGTACTG CAGGTGTTAT GCCATAAAGAC
(SEQ ID NO:26) CACTGCATGAC GTCCACAATA CGGTATTTCAG (SEQ ID NO:27) TTCACTGGCGA CTTCTCGTCT AGGTTGGGATT
(SEQ ID NO:5) AAGTGACCGCT GAAGAGCAGA TCCAACCCTAA

FIG. 8

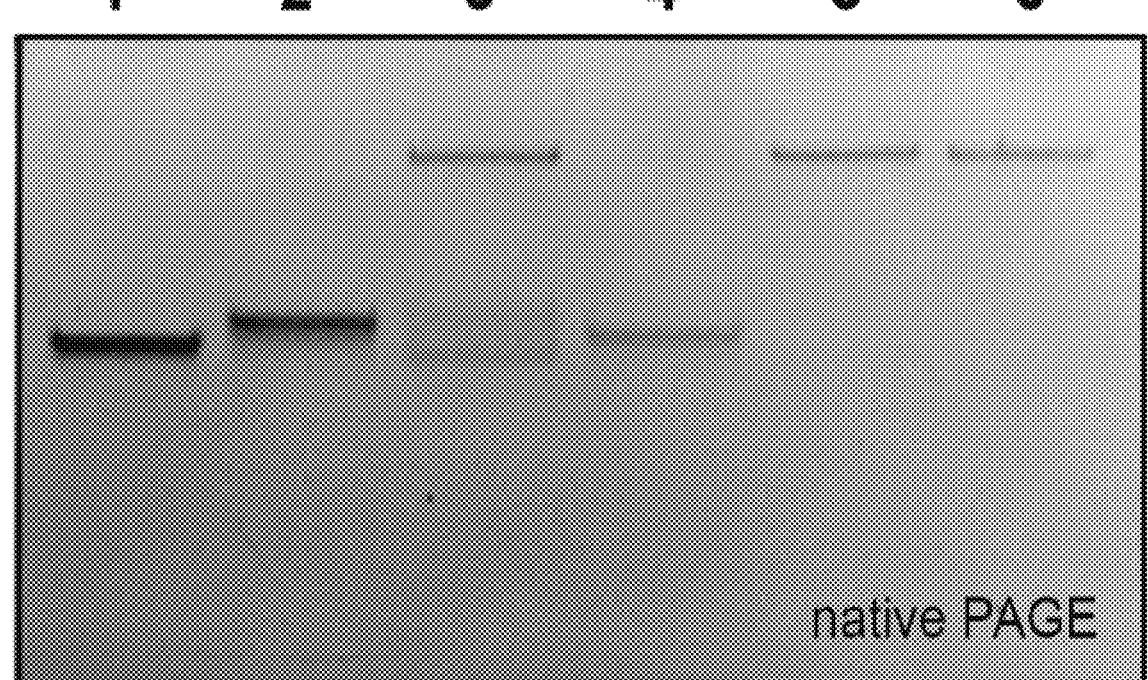

native PAGE

SEQUENCE LISTING

```
Sequence total quantity: 31
SEQ ID NO: 1              moltype = AA   length = 10
FEATURE                  Location/Qualifiers
source                   1..10
                         mol_type = protein
                         organism = synthetic construct
SEQUENCE: 1
GGPQGIWGQG                                                         10

SEQ ID NO: 2              moltype = AA   length = 10
FEATURE                  Location/Qualifiers
source                   1..10
                         mol_type = protein
                         organism = synthetic construct
SEQUENCE: 2
GQGIPQGWGG                                                         10

SEQ ID NO: 3              moltype = AA   length = 6
FEATURE                  Location/Qualifiers
source                   1..6
                         mol_type = protein
                         organism = synthetic construct
SEQUENCE: 3
GRGDSG                                                             6

SEQ ID NO: 4              moltype = DNA   length = 32
FEATURE                  Location/Qualifiers
source                   1..32
                         mol_type = other DNA
                         organism = synthetic construct
SEQUENCE: 4
```

```
cagaaatacc gtattgtgga cgtcatgcag tg                                  32

SEQ ID NO: 5             moltype = DNA   length = 32
FEATURE                  Location/Qualifiers
source                   1..32
                         mol_type = other DNA
                         organism = synthetic construct
SEQUENCE: 5
aagtgaccgc tgaagagcag atccaaccct aa                                  32

SEQ ID NO: 6             moltype = DNA   length = 20
FEATURE                  Location/Qualifiers
source                   1..20
                         mol_type = other DNA
                         organism = synthetic construct
SEQUENCE: 6
tcttcgtcca caatatctgc                                                20

SEQ ID NO: 7             moltype = DNA   length = 22
FEATURE                  Location/Qualifiers
source                   1..22
                         mol_type = other DNA
                         organism = synthetic construct
SEQUENCE: 7
cactgcatga cagcggtcac tt                                             22

SEQ ID NO: 8             moltype = DNA   length = 22
FEATURE                  Location/Qualifiers
source                   1..22
                         mol_type = other DNA
                         organism = synthetic construct
SEQUENCE: 8
ttagggttgg acggtatttc ag                                             22

SEQ ID NO: 9             moltype = DNA   length = 32
FEATURE                  Location/Qualifiers
source                   1..32
                         mol_type = other DNA
                         organism = synthetic construct
SEQUENCE: 9
cactgcatgc atcgctccgt taatgctttc cc                                  32

SEQ ID NO: 10            moltype = DNA   length = 32
FEATURE                  Location/Qualifiers
source                   1..32
                         mol_type = other DNA
                         organism = synthetic construct
SEQUENCE: 10
agcgagacct ccctgacagt aatttgaggg ct                                  32

SEQ ID NO: 11            moltype = DNA   length = 20
FEATURE                  Location/Qualifiers
source                   1..20
                         mol_type = other DNA
                         organism = synthetic construct
SEQUENCE: 11
tcaggaacgg agcgatactg                                                20

SEQ ID NO: 12            moltype = DNA   length = 22
FEATURE                  Location/Qualifiers
source                   1..22
                         mol_type = other DNA
                         organism = synthetic construct
SEQUENCE: 12
gggaaagcat tgaggtctcg ct                                             22

SEQ ID NO: 13            moltype = DNA   length = 22
FEATURE                  Location/Qualifiers
source                   1..22
                         mol_type = other DNA
                         organism = synthetic construct
SEQUENCE: 13
agccctcaaa ttgcatgcag tg                                             22

SEQ ID NO: 14            moltype = DNA   length = 16
FEATURE                  Location/Qualifiers
source                   1..16
                         mol_type = other DNA
                         organism = synthetic construct
```

-continued

```
SEQUENCE: 14
cgtattcgac tgggtg                                            16

SEQ ID NO: 15          moltype = DNA   length = 32
FEATURE                Location/Qualifiers
source                 1..32
                       mol_type = other DNA
                       organism = synthetic construct
SEQUENCE: 15
aagtgaccgc tcagtccgaa gagaatcgag cc                          32

SEQ ID NO: 16          moltype = DNA   length = 20
FEATURE                Location/Qualifiers
source                 1..20
                       mol_type = other DNA
                       organism = synthetic construct
SEQUENCE: 16
gactgatacg aaggccttcg                                        20

SEQ ID NO: 17          moltype = DNA   length = 22
FEATURE                Location/Qualifiers
source                 1..22
                       mol_type = other DNA
                       organism = synthetic construct
SEQUENCE: 17
cacccagtcg aagcggtcac tt                                     22

SEQ ID NO: 18          moltype = DNA   length = 22
FEATURE                Location/Qualifiers
source                 1..22
                       mol_type = other DNA
                       organism = synthetic construct
SEQUENCE: 18
ggctcgattc taccgacgtc cg                                     22

SEQ ID NO: 19          moltype = DNA   length = 16
FEATURE                Location/Qualifiers
source                 1..16
                       mol_type = other DNA
                       organism = synthetic construct
SEQUENCE: 19
cggacgtcgg tgcctt                                            16

SEQ ID NO: 20          moltype = DNA   length = 22
FEATURE                Location/Qualifiers
source                 1..22
                       mol_type = other DNA
                       organism = synthetic construct
SEQUENCE: 20
ttcactggcg acagtacgtc ac                                     22

SEQ ID NO: 21          moltype = DNA   length = 22
FEATURE                Location/Qualifiers
source                 1..22
                       mol_type = other DNA
                       organism = synthetic construct
SEQUENCE: 21
gtgacgtacg ttaaactccc ga                                     22

SEQ ID NO: 22          moltype = DNA   length = 32
FEATURE                Location/Qualifiers
source                 1..32
                       mol_type = other DNA
                       organism = synthetic construct
SEQUENCE: 22
ccctttcgta attgcctcgc tacgtacgtc ac                          32

SEQ ID NO: 23          moltype = DNA   length = 32
FEATURE                Location/Qualifiers
source                 1..32
                       mol_type = other DNA
                       organism = synthetic construct
SEQUENCE: 23
gggaaagcat taacggagcg atgcatgcag tg                          32

SEQ ID NO: 24          moltype = DNA   length = 32
FEATURE                Location/Qualifiers
source                 1..32
                       mol_type = other DNA
```

-continued

```
                              organism = synthetic construct
SEQUENCE: 24
tcgctctgga gggactgtca ttaaactccc ga                               32

SEQ ID NO: 25          moltype = DNA   length = 32
FEATURE                Location/Qualifiers
source                 1..32
                       mol_type = other DNA
                       organism = synthetic construct
SEQUENCE: 25
gtgacgtact gcaggtgtta tgccataaag ac                               32

SEQ ID NO: 26          moltype = DNA   length = 32
FEATURE                Location/Qualifiers
source                 1..32
                       mol_type = other DNA
                       organism = synthetic construct
SEQUENCE: 26
cactgcatga cgtccacaat acggtatttc ag                               32

SEQ ID NO: 27          moltype = DNA   length = 32
FEATURE                Location/Qualifiers
source                 1..32
                       mol_type = other DNA
                       organism = synthetic construct
SEQUENCE: 27
ttcactggcg acttctcgtc taggttggga tt                               32

SEQ ID NO: 28          moltype = DNA   length = 16
FEATURE                Location/Qualifiers
source                 1..16
                       mol_type = other DNA
                       organism = synthetic construct
SEQUENCE: 28
ttccgtggct gcaggc                                                 16

SEQ ID NO: 29          moltype = DNA   length = 32
FEATURE                Location/Qualifiers
source                 1..32
                       mol_type = other DNA
                       organism = synthetic construct
SEQUENCE: 29
gtgggtcagc ttatgcttcc gtggctgcag gc                               32

SEQ ID NO: 30          moltype = DNA   length = 32
FEATURE                Location/Qualifiers
source                 1..32
                       mol_type = other DNA
                       organism = synthetic construct
SEQUENCE: 30
cacccagtcg aatacgaagg caccgacgtc cg                               32

SEQ ID NO: 31          moltype = DNA   length = 32
FEATURE                Location/Qualifiers
source                 1..32
                       mol_type = other DNA
                       organism = synthetic construct
SEQUENCE: 31
ttcactggcg agtcaggctt ctcttagctc gg                               32
```

NUCLEIC ACID-PEPTIDE-NUCLEIC ACID CONJUGATE MOLECULES AND METHODS OF MAKING THE SAME

CROSS-REFERENCE TO RELATED APPLICATIONS

The present application claims priority to U.S. Provisional Patent Application No. 63/231,974, filed Aug. 11, 2021, the entire contents of which are hereby incorporated by reference.

STATEMENT REGARDING FEDERALLY SPONSORED RESEARCH

This invention was made with government support under GM132931 awarded by the National Institutes of Health. The Government has certain rights in the invention.

REFERENCE TO A SEQUENCE LISTING

A Sequence Listing accompanies this application and is submitted as an XML file of the sequence listing named "112624.01356.xml" which is 28,281 bytes in size and was created on Aug. 8, 2022. The sequence listing is electronically submitted via Patent Center with the application and is incorporated herein by reference in its entirety.

FIELD OF INVENTION

The present disclosure generally relates to nucleic acid-peptide-nucleic acid conjugate molecules, and to methods of making nucleic acid-peptide-nucleic acid conjugate molecules using proximity-enhanced synthesis. Also disclosed herein are exemplary applications of such nucleic acid-peptide-nucleic acid conjugate molecules for drug delivery, molecular assembly of hybrid materials, and constraining the peptide to a biologically active conformation.

BACKGROUND

The ability to chemically modify synthetic peptides with programmable oligonucleotide handles has led to hybrid materials with applications in DNA and RNA delivery, dynamic biomaterials, and hybrid self-assembling nanomaterials. The peptide component may impart biological activity such as, but not limited to, cell targeting, endosomal escape, cell surface receptor engagement, or enzymatic responsiveness. The oligonucleotide component, by contrast, allows for attachment of a complementary cargo (e.g., siRNA or other cargo molecule comprising a region complementary to the oligonucleotide), dynamic exchange via toehold displacement, or immobilization of the peptide on a DNA nanostructure. Few examples exist of attaching two different, orthogonal oligonucleotide handles to either side of a peptide with site-specificity. Such triblock molecules can enable unique applications. For example, peptides flanked by two peptide nucleic acid (PNA) handles have been used for reversibly switching the peptide activity via conformational control imposed by the oligonucleotide scaffold, as molecular beacons for biosensing, or cleavable reporters of protease activity. Other recent results suggest that DNA-peptide-DNA (DPD) triblock molecules could serve as monomers for full-length protein synthesis through an oligonucleotide-templated mechanism, reminiscent of the ribosome. However, the preparation of peptides having two different, orthogonal oligonucleotide handles remains a challenge in practice.

Thus, due to the landscape of potential applications, there is a need for improved strategies for preparing nucleic acid-peptide-nucleic acid triblock molecules.

SUMMARY

Disclosed herein are nucleic acid-peptide-nucleic acid conjugate molecules, and methods for synthesizing nucleic acid-peptide-nucleic acid conjugate molecules using proximity-enhanced synthesis. Also disclosed herein are applications of such nucleic acid-peptide-nucleic acid conjugate molecules for drug delivery, molecular assembly of hybrid structures, and synthesis of alternating (peptide-nucleic acid)N copolymers. In some embodiments, the peptide of the nucleic acid-peptide-nucleic acid conjugate molecule is a substrate for enzymatic cleavage.

Disclosed herein are methods for synthesizing a nucleic acid-peptide-nucleic acid conjugate molecule. In some embodiments, the methods comprise covalently linking a peptide with a first nucleic acid strand via a first reaction to provide a nucleic acid-peptide conjugate, hybridizing the first nucleic acid strand of the nucleic acid-peptide conjugate with a second nucleic acid strand to bring the second nucleic acid strand in proximity to the peptide, and covalently linking the peptide with the second nucleic acid strand via a second reaction to provide the nucleic acid-peptide-nucleic acid conjugate molecule. In some embodiments, the first reaction and the second reaction are orthogonal chemical reactions.

Further disclosed herein is a nucleic acid-peptide-nucleic acid conjugate molecule. The nucleic acid-peptide-nucleic acid conjugate molecule includes a peptide having an N-terminal end and a C-terminal end, a first nucleic acid strand covalently linked to the peptide at the N-terminal end, and a second nucleic acid strand covalently linked to the peptide at the C-terminal end. In some embodiments, the first nucleic acid strand and the second nucleic acid strand are at least partially hybridized, thereby constraining the nucleic acid-peptide-nucleic acid conjugate molecule to a hairpin structure.

Also disclosed herein is a drug delivery vehicle. In some embodiments, the drug delivery vehicle comprises a nucleic acid-based nano-container, a therapeutic agent within the nucleic acid-based nano-container, and a nucleic acid-peptide-nucleic acid conjugate including a peptide modified with a first nucleic acid strand and a second nucleic acid strand. In some embodiments, the first nucleic acid strand and the second nucleic acid strand are hybridized with complementary nucleic acid strands of the nucleic acid-based nano-container to secure the therapeutic agent within the nucleic acid-based nano-container.

Further disclosed herein are methods of drug delivery comprising encapsulating a therapeutic agent inside of a nucleic acid-based nano-container, and securing the therapeutic agent inside of the nucleic acid-based nano-container with a nucleic acid-peptide-nucleic acid conjugate molecule having at least a first nucleic acid strand and a second nucleic acid strand that hybridize with complementary nucleic acid strands of the nucleic acid-based nano-container. In some embodiments, the method further comprises degrading the peptide to release the therapeutic agent from the nucleic acid-based nano-container.

Further disclosed herein is a molecular assembly comprising a nucleic acid-peptide-nucleic acid conjugate molecule having a peptide modified with a first nucleic acid strand and a second nucleic acid strand. In some embodiments, the first nucleic acid strand is hybridized with a first complementary nucleic acid strand of a DNA double crossover tile, and the second nucleic acid strand is hybridized with a second complementary nucleic acid strand of the DNA double crossover tile. In some embodiments, the peptide is constrained to a loop conformation in the molecular assembly.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention FIG. 1: Synthesis of DNA-peptide-DNA triblock molecules. Panel A) shows initial attempts to synthesize a DNA-peptide-DNA ("DPD") triblock molecule. A peptide modified with an N-terminal azidolysine (azK) and a C-terminal propargylalanine (prA) was modified with DNA1-dibenzocyclooctyne (DBCO) using strain-promoted azide-alkyne cycloaddition (SPAAC, step (i)). This conjugate was then exposed to DNA2-azide and conditions for copper(I)-catalyzed azide-alkyne cycloaddition (CuAAC, step (ii)), but this step was unsuccessful. Panel B) shows proximity-aided CuAAC, whereby the DNA1-peptide-(prA) conjugate is partially complementary to the DNA2-azide molecule. Hybridization by annealing and subsequent exposure to CuAAC conditions results in a DPD hairpin with single-stranded (ss) DNA overhangs for eventual strand displacement. Arrows represent the 3' end of the DNA strands. SEQ ID NOs 20, 21 and 7 are shown in FIG. 1B.

FIG. 7: Confirmation that the DX tiles are stable at the optimal incubation temperature of matrix metalloproteinase (37° C.). The bands run at the same retention as tiles incubated at RT, so the elevated temperature does not affect them. Sample (1) is an all-DNA tile, and (2) contains the DNA1-MMP$_{pep}$ conjugate. SEQ ID NOs 22, 23, 24, 10, 25, 26, 27 and 5 are shown in FIG. 7.

FIG. 8: Confirmation that the MMP$_{pep}$ sequence is required for MMP8 cleavage of a DX tile dimer. Lanes 1-4 correspond to the same samples as FIG. 3A: individual tiles (lanes 1 and 2), the tile dimer before (lane 3) and after (lane 4) exposure to MMP8. Lanes 5 and 6 are a tile dimer linked by MMP$_{pep-scram}$ before (lane 5) and after (lane 6) exposure to MMP8.

DETAILED DESCRIPTION

Terminology

Figure 2:
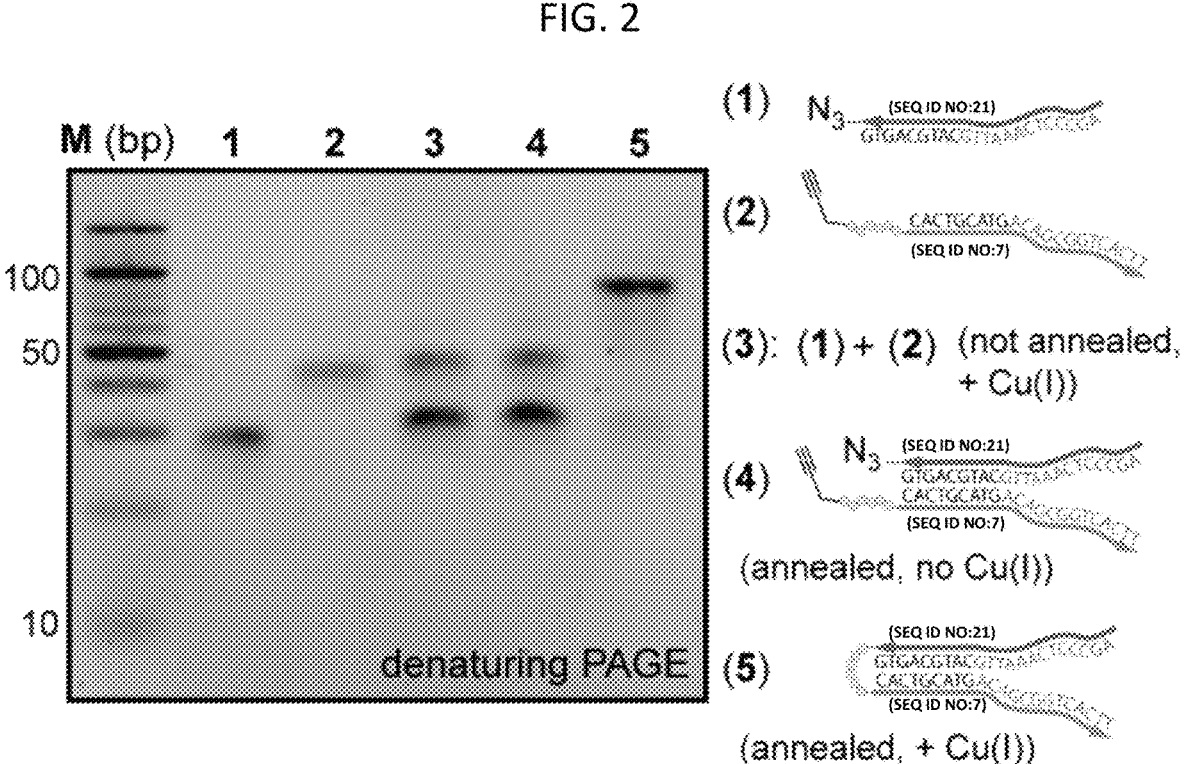
FIG. 2: Gel electrophoresis analysis of triblock synthesis. Denaturing PAGE of indicated systems. Lane M: ssDNA ladder (bp); 1: DNA2-azide; 2: DNA1-MMP$_{pep}$-(prA) conjugate; 3: DNA2-azide+DNA1-MMP$_{pep}$-(prA), without annealing, but exposed to CuAAC conditions. 4,5: DNA2-azide+DNA1-MMP$_{pep}$-(prA), annealed, before (lane 4) and after (lane 5) exposure to CuAAC conditions. SEQ ID NOs 21 and 7 are shown in FIG. 2.

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the term "nanostructure" is a defined structure having at least one dimension (e.g., length, width, thickness) in the nanoscale range (approximately 1 nanometer (nm) to 100 nm).

As used herein, the term "polypeptide" is a polymer of amino acids linked together by peptide bonds. A "polypeptide", as used herein, includes synthetic polypeptides, naturally-occurring polypeptides, and polypeptides that form part of (or the whole of) protein molecules. This term refers to polypeptides having one or more of random coil structures, secondary structures (e.g., alpha-helix, beta-sheet), and tertiary structures, as well as combinations thereof. The amino acids of the polypeptide may include naturally occurring amino acids, unnatural or synthetic amino acids, and combinations thereof.

As used herein, the term "nucleic acid" refers to a polymer of nucleic acid bases such as oligonucleotides including single-stranded DNA, double-stranded DNA, RNA, aptamers, and peptide nucleic acids (PNAs). The nucleic acid bases may include natural nucleic acid bases (e.g., adenine, guanine, cytosine, thymine, uracil), unnatural nucleic acid bases, or combinations thereof.

As used herein, the term "nucleic acid-peptide-nucleic acid conjugate molecule" is a block copolymer composed of a polypeptide modified with at least two separate polynucleic acid strands.

The term "orthogonal chemical reactions", as used herein, refers to chemical reactions that occur selectively and in high yield in the presence of other functional groups. Exemplary orthogonal reactions include, but are not limited to, click chemistry including strain-promoted azide-alkyne cycloaddition (SPAAC) and copper(I)-catalyzed azide-alkyne cycloaddition (CuAAC), maleimide chemistry, disulfide formation, oxime formation between an aminooxy group and a ketone/aldehyde, tetrazine/trans-cyclooctene conjugation, enzymatic ligations (e.g., transglutaminase), copper-catalyzed click reactions, and tyrosine oxidation reactions. Various other reactions may include those described in Stephanopoulos, N., "Hybrid Nanostructures from the Self-Assembly of Proteins and DNA", Chem, 6, pp. 364-405, 2020, incorporated herein by reference.

As used herein, the term "drug delivery vehicle" is a molecular assembly or structure carrying at least one therapeutic agent and having a defined mechanism or stimulus for triggering release of the therapeutic agent.

As used herein, the term "nucleic acid-based nano-container" is a molecular container at least partially composed of self-assembled nucleic acids, and having at least one dimension (e.g., length, width, thickness) in the nanoscale range (approximately 1 nanometer (nm) to 100 nm).

As used herein, the term "DNA double crossover tile" is a DNA assembly composed of DNA strands forming two duplexes which are connected by two crossover junctions.

As used herein, the term "drug" is used interchangeably with "therapeutic," and refers to a composition or component of a composition, comprising a small molecule, antibody or fragment thereof, peptide, nucleic acid, etc. that has a therapeutic effect when administered to a subject in need thereof, e.g., a subject suffering from a disease or condition. In some embodiments, a drug comprises, or is a nucleic acid, such as DNA, or such as an RNA, e.g., siRNA or shRNA. By way of example but not by way of limitation, a therapeutic molecule may be a peptide or other small molecule, and the peptide or other small molecule may be linked to one or more nucleic acids. In some embodiments, the drug is a nucleic acid molecule.

Proximity-Enhanced Synthesis of DNA-Peptide-DNA Triblock Molecules

Disclosed herein is a DNA nano-container bearing a therapeutic cargo and secured with a degradable peptide that can serve as a stimulus-responsive delivery vehicle. In some embodiments, the degradable peptide is a substrate for enzymatic cleavage. In some embodiments, the degradable peptide is a substrate for matrix metalloproteinase-8 (MMP-8) cleavage. In some embodiments, the degradable peptide may be a substrate for cleavage by proteases such as, but not limited to, pepsin, trypsin, thermolysin, papain, and TEV protease. The structure form is defined as a triblock molecule: DNA-peptide-DNA. This technology has the potential to serve as enzymatically-cleavable peptide latches for oligonucleotide structures, or as logic-gated degradable crosslinks for hydrogels.

Further disclosed herein are methods to create these triblock molecules. The peptide sequence (prA)GGPQGIWGQG(azK) (SEQ ID NO:1) is identified as an exemplary substrate for matrix metalloproteinase-8 (MMP8), wherein prA is a propargyl alanine residue and azK is an azidolysine residue. The two noncanonical amino acids allow for sequential, orthogonal azide-alkyne cycloaddition reactions. DNA1 and DNA2 of the triblock molecule are partially complementary to form a hairpin structure.

In one exemplary embodiment, the synthesis of a DNA-peptide-DNA (DPD) triblock molecule involves modifying the peptide with an N-terminal azidolysine (azK) and a C-terminal propargyl alanine (prA). In one embodiment, the peptide is (prA)GGPQGIWGQG(azK) (SEQ ID NO:1). In another embodiment, the peptide is (prA)GRGDSG(azK) (SEQ ID NO:3). This peptide is modified with DNA1-dibenzocyclooctyne (DBCO) using strain-promoted azide-alkyne cycloaddition (SPAAC). The resulting DNA-peptide-prA conjugate is partially complementary to the DNA2-azide molecule. Hybridization by annealing and subsequent exposure to copper(I)-catalyzed azide-alkyne cycloaddition (CuAAC) conditions results in a DPD hairpin with single-stranded DNA overhangs for eventual strand displacement.

EXEMPLARY EMBODIMENTS

Provided below are several, non-limiting exemplary embodiments of the compositions, methods, and systems disclosed herein.

1. A method for synthesizing a nucleic acid-peptide-nucleic acid conjugate molecule, comprising: covalently linking a peptide with a first nucleic acid strand via a first reaction to provide a nucleic acid-peptide conjugate; hybridizing the first nucleic acid strand of the nucleic acid-peptide conjugate with a second nucleic acid strand to bring a second nucleic acid strand in proximity to the peptide; and covalently linking the peptide with the second nucleic acid strand via a second reaction to provide the nucleic acid-peptide-nucleic acid conjugate molecule, wherein the first reaction and the second reaction are orthogonal chemical reactions.

2. The method of embodiment 1, wherein the first nucleic acid strand and the second nucleic acid strand have different nucleic acid sequences and are not fully complementary.

3. The method of embodiment 1, wherein the first reaction and the second reaction are orthogonal azide-alkyne cycloaddition reactions.

4. The method of embodiment 1, wherein the first reaction is a strain-promoted azide-alkyne cycloaddition (SPAAC) reaction, and the second reaction is a copper(I)-catalyzed azide-alkyne cycloaddition (CuAAC) reaction.

5. The method of embodiment 4, wherein the peptide is modified with an N-terminal or C-terminal azide group, wherein the first nucleic acid strand is modified with a dibenzocyclooctyne group, and wherein the azide group of the peptide reacts with the dibenzocyclooctyne group of the first nucleic acid strand via the SPAAC reaction.

6. The method of embodiment 5, wherein the peptide is modified with an N-terminal or C-terminal alkyne group, wherein the second nucleic acid strand is modified with an azide group, and wherein the alkyne group of the peptide reacts with the azide group of the second nucleic acid strand via the CuAAC reaction.

7. The method of embodiment 1, wherein the first nucleic acid strand and the second nucleic acid strand are partially hybridized in the nucleic acid-peptide-nucleic acid conjugate molecule.

8. The method of embodiment 7, wherein the nucleic acid-peptide-nucleic acid conjugate molecule includes single-stranded overhangs where the first nucleic acid strand and the second nucleic acid strand are unhybridized.

9. The method of embodiment 7, wherein the nucleic acid-peptide-nucleic acid conjugate molecule is constrained to a hairpin structure by the partial hybridization between the first nucleic acid strand and the second nucleic acid strand.

10. The method of embodiment 9, further comprising displacing the first nucleic acid strand from the second nucleic acid strand using one or more single-stranded nucleic acid strands that are fully complementary to the first nucleic acid strand and/or the second nucleic acid strand.

11. The method of embodiment 10, wherein displacing the first nucleic acid strand from the second nucleic acid strand disrupts the hairpin structure of the nucleic acid-peptide-nucleic acid conjugate molecule.

12. The method of embodiment 1, wherein the peptide is a substrate for enzymatic cleavage, and optionally cleaving the peptide with the enzyme.

13. The method of embodiment 1, wherein the peptide is a substrate for matrix metalloproteinase-8 (MMP-8), and wherein the method further comprises cleaving the peptide with MMP-8.

14. The method of embodiment 12, further comprising hybridizing the nucleic acid-peptide-nucleic acid conjugate molecule to complementary nucleic acid strands of a nucleic acid-based container carrying a therapeutic agent to secure the therapeutic agent inside of the nucleic acid-based container.

15. The method of embodiment 14, further comprising cleaving the peptide of the nucleic acid-peptide-nucleic acid conjugate with the enzyme to release the therapeutic molecule from the nucleic acid-based container.

16. The method of embodiment 15, wherein the peptide is a substrate for matrix metalloproteinase-8 (MMP-8), and wherein cleaving the peptide comprises cleaving the peptide with MMP-8.

17. The method of embodiment 1, further comprising hybridizing the first nucleic acid strand of the nucleic acid-peptide-nucleic acid conjugate molecule with a complementary nucleic acid strand of a first nucleic acid-based nanostructure; and hybridizing the second nucleic acid strand of the nucleic acid-peptide-nucleic acid conjugate molecule with a complementary nucleic acid strand of a second nucleic acid-based nanostructure to link the first nucleic acid-based nanostructure to the second nucleic acid-based nanostructure.

18. The method of embodiment 17, wherein the first nucleic acid-based nanostructure is a DNA double crossover tile, and wherein the second nucleic acid-based nanostructure is a DNA double crossover tile.

19. A method for synthesizing a nucleic acid-peptide-nucleic acid conjugate molecule, comprising providing a peptide having a first reactive group and a second reactive group; covalently linking the peptide with a first nucleic acid strand by reacting the first reactive group of the peptide with a third reactive group of the first nucleic acid strand; hybridizing a second nucleic acid strand having a fourth reactive group with the first nucleic acid strand to bring the fourth reactive group in proximity to the second reactive group of the peptide; and covalently linking the peptide with the second nucleic acid strand by reacting the second reactive group of the peptide with the fourth reactive group of the second nucleic acid strand to provide the nucleic acid-peptide-nucleic acid conjugate molecule.

20. The method of embodiment 19, wherein the first reactive group is an azide group; the second reactive group is an alkyne group; the third reactive group of the first nucleic acid strand is a dibenzocyclooctyne group; the fourth reactive group of the second nucleic acid strand is an azide group; covalently linking the peptide with the first nucleic acid strand comprises reacting the peptide with the first nucleic acid strand by a strain-promoted azide-alkyne cycloaddition (SPAAC) reaction; and covalently linking the peptide with the second nucleic acid strand comprises reacting the peptide with the second nucleic acid strand by a copper(I)-catalyzed azide-alkyne cycloaddition (CuAAC) reaction.

21. The method of embodiment 19, wherein the first reactive group is at an N-terminal end of the peptide, and wherein the second reactive group is at a C-terminal end of the peptide.

22. A method for synthesizing a nucleic acid-peptide-nucleic acid conjugate molecule, comprising: covalently linking a peptide with a first nucleic acid strand via a first reaction to provide a nucleic acid-peptide conjugate; hybridizing the first nucleic acid strand of the nucleic acid-peptide conjugate with a complementary strand of a nucleic acid-based nanostructure to bring the peptide in proximity to a second nucleic acid strand of the nucleic acid-based nanostructure; and covalently linking the peptide with the second nucleic acid strand via a second reaction to provide the nucleic acid-peptide-nucleic acid conjugate molecule, wherein the first reaction and the second reaction are orthogonal chemical reactions.

23. A nucleic acid-peptide-nucleic acid conjugate molecule, comprising: a peptide having an N-terminal end and a C-terminal end; a first nucleic acid strand covalently linked to the peptide at the N-terminal end; and a second nucleic acid strand covalently linked to the peptide at the C-terminal end, wherein the first nucleic acid strand and the second nucleic acid strand are at least partially hybridized, thereby constraining the nucleic acid-peptide-nucleic acid conjugate molecule to a hairpin structure.

24. The nucleic acid-peptide-nucleic acid conjugate molecule of embodiment 23, wherein the first nucleic acid strand and the second nucleic acid strand have different nucleic acid sequences.

25. The nucleic acid-peptide-nucleic acid conjugate molecule of embodiment 23, wherein the peptide is an integrin-binding peptide.

26. The nucleic acid-peptide-nucleic acid conjugate molecule of embodiment 23, wherein the peptide is a substrate for enzymatic cleavage.

27. The nucleic acid-peptide-nucleic acid conjugate molecule of embodiment 23, wherein the peptide is a substrate for cleavage by matrix metalloproteinase-8.

28. The nucleic acid-peptide-nucleic acid conjugate molecule of embodiment 23, wherein the first nucleic acid strand and the peptide are covalently linked by a first azide-alkyne cycloaddition reaction, and wherein the second nucleic acid strand and the peptide are covalently linked by a second azide-alkyne cycloaddition reaction.

29. The nucleic acid-peptide-nucleic acid conjugate molecule of embodiment 28, wherein the first azide-alkyne cycloaddition reaction is a strain-promoted azide-alkyne cycloaddition (SPAAC) reaction, and wherein the second azide-alkyne cycloaddition reaction is a copper(I)-catalyzed azide-alkyne cycloaddition (CuAAC) reaction.

30. A drug delivery vehicle, comprising: a nucleic acid-based nano-container; a therapeutic agent within the nucleic acid-based nano-container; and a nucleic acid-peptide-nucleic acid conjugate including a peptide modified with a first nucleic acid strand and a second nucleic acid strand, the first nucleic acid strand and the second nucleic acid strand being hybridized with complementary nucleic acid strands of the nucleic acid-based nano-container to secure the therapeutic agent within the nucleic acid-based nano-container.

31. The drug delivery vehicle of embodiment 30, wherein the first nucleic acid strand is coupled at an N-terminal end of the peptide, and wherein the second nucleic acid strand is coupled at a C-terminal end of the peptide.

32. The drug delivery vehicle of embodiment 30, wherein the first nucleic acid strand and the second nucleic acid strand have different sequences.

33. The drug delivery vehicle of embodiment 30, wherein the peptide is a substrate for enzymatic cleavage.

34. The drug delivery vehicle of embodiment 33, wherein cleavage of the peptide with an enzyme triggers release of the therapeutic agent from the nucleic acid-based nano-container.

35. The drug delivery vehicle of embodiment 30, wherein the peptide is a substrate for matrix metalloproteinase-8 (MMP8), and wherein cleavage of the peptide with MMP8 triggers release of the therapeutic agent from the nucleic acid-based nano-container.

36. A method of drug delivery, comprising encapsulating a therapeutic agent inside of a nucleic acid-based nano-container; securing the therapeutic agent inside of the nucleic acid-based nano-container with a nucleic acid-peptide-nucleic acid conjugate molecule having at least a first nucleic acid strand and a second nucleic acid strand that hybridize with complementary nucleic acid strands of the nucleic acid-based nano-container; and degrading the peptide to release of the therapeutic agent from the nucleic acid-based nano-container.

37. The method of embodiment 36, wherein the peptide is a substrate for enzymatic cleavage, and wherein degrading the peptide comprises cleaving the peptide with the enzyme.

38. The method of drug delivery of embodiment 37, wherein the peptide is a substrate for matrix metalloproteinase-8 (MMP8), and wherein degrading the peptide comprises cleaving the peptide with MMP8.

39. A molecular assembly, comprising: a first nucleic acid-based structure; a second nucleic acid-based structure; and a nucleic acid-peptide-nucleic acid conjugate molecule including a peptide modified with a first nucleic acid strand and a second nucleic acid strand; wherein the first nucleic acid strand is hybridized with a complementary nucleic acid strand of the first nucleic acid-based structure, and the second nucleic acid strand is hybridized with a complementary nucleic acid strand of the second nucleic acid-based structure such that the nucleic acid-peptide-nucleic acid conjugate molecule links the first nucleic acid-based structure and the second nucleic acid-based structure.

40. The molecular assembly of embodiment 39, wherein the peptide is a substrate for enzymatic cleavage.

41. The molecular assembly of embodiment 39, wherein the peptide is a substrate for cleavage by matrix metalloproteinase-8 (MMP8).

42. The molecular assembly of embodiment 39, wherein the first nucleic acid-based structure is a DNA double crossover tile having two crossover strands; the second nucleic acid-based structure is a DNA double crossover tile having two crossover strands; the first nucleic acid strand of the nucleic acid-peptide-nucleic acid conjugate molecule serves as one of the two crossover strands of the first nucleic acid-based structure; and the second nucleic acid strand of the nucleic acid-peptide-nucleic acid conjugate molecule serves as one of the two crossover strands of the second nucleic acid-based structure.

43. The molecular assembly of embodiment 42, wherein the molecular assembly is a dimer of the DNA double crossover tiles linked by the nucleic acid-peptide-nucleic acid conjugate molecule.

44. A molecular assembly comprising a nucleic acid-peptide-nucleic acid conjugate molecule having a peptide modified with a first nucleic acid strand and a second nucleic acid strand, wherein the first nucleic acid strand is hybridized with a first complementary nucleic acid strand of a DNA double crossover tile, wherein the second nucleic acid strand is hybridized with a second complementary nucleic acid strand of the DNA double crossover tile, and wherein the peptide is constrained to a loop conformation in the molecular assembly.

45. The molecular assembly of embodiment 44, wherein the peptide is an integrin-binding peptide.

EXAMPLES

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Example 1

Proximity-Enhanced Synthesis of DNA-Peptide-DNA Triblock Molecules

The ability to chemically modify synthetic peptides with programmable oligonucleotide handles has led to hybrid materials with applications in DNA and RNA delivery, dynamic biomaterials, and hybrid self-assembling nanomaterials. The peptide component imparts biological activity, such as cell targeting, endosomal escape, cell surface receptor engagement, or enzymatic responsiveness. The oligonucleotide component allows for attachment of a complementary cargo (e.g. siRNA), dynamic exchange via toehold displacement, or immobilization of the peptide on a DNA nanostructure. Far fewer examples exist, however, of attaching two different, orthogonal oligonucleotide handles to either side of a peptide, with site-specificity. However, such triblock molecules can enable unique applications if the oligonucleotides are partially complementary, resulting in a hairpin structure. For example, peptides flanked by two peptide nucleic acid (PNA) handles have been used to reversibly switching the peptide activity through conformational control imposed by the oligonucleotide scaffold, and as molecular beacons for biosensing or cleavable reporters of protease activity. In one recent report, peptides flanked by two orthogonal DNA handles attached via a photocleavable linker could be linked into sequence-defined polypeptides through proximity-aided amide formation followed by light-induced removal of the DNA strands. Thus, DNA-peptide- DNA (DPD) triblock molecules could, in principle, serve as monomers for full-length protein synthesis, through an oligonucleotide-templated mechanism reminiscent of the ribosome.

In addition to these applications, DPD molecules are useful as enzymatically-cleavable peptide "latches" for oligonucleotide nanostructures (e.g. a DNA origami nanorobot), or as "logic-gated" degradable crosslinks for hydrogels. Matrix metalloproteinase enzymes like MMP8, in particular, are known to be overexpressed in the tumor microenvironment. Thus, a DNA nano-container bearing a therapeutic cargo, and secured with an MMP-degradable peptide, could serve as a stimulus-responsive delivery vehicle. Towards this end, we synthesized the peptide (prA) GGPQGIWGQG(azK) (SEQ ID NO:1), a substrate for matrix metalloproteinase 8 (MMP8), using solid-phase peptide synthesis. This peptide (which we term $MMP_{pep}$) includes two noncanonical amino acids for sequential, orthogonal DNA coupling reactions (FIG. 1A): (1) a C-terminal azidolysine (azK) for strain-promoted azide-alkyne cycloaddition (SPAAC) with DNA1 modified with dibenzocyclooctyne (DBCO); and (2) an N-terminal propargylalanine (prA) for copper(I)-catalyzed azide-alkyne cycloaddition (CuAAC) with DNA2 modified with an azide. Here, "DNA1" and "DNA2" refer to two different DNA sequences, each 22 nucleotides in length. Although the synthesis of DNA1-$MMP_{pep}$-(prA) proceeded smoothly and in high yield via SPAAC, according to previously developed protocols in our lab, in our hands the subsequent CuAAC reaction was unsuccessful. We screened a range of conditions that varied the alkyne:azide ratio, the overall Cu(I) concentration, different ligands, and a range of reaction times, including the conditions used in the previous report of a DPD synthesis, but in our hands the yield of the desired triblock molecule was negligible. It is well documented in the art that while CuAAC chemistry has a number of optimizable reaction conditions and stoichiometries, other factors, including steric hindrance of reactive groups, may prevent bond formation.

We reasoned that the yield of the second bioconjugation reaction could be enhanced if the two reactive ends (the N-terminal alkyne on the DNA1-$MMP_{pep}$-(prA) conjugate, and the azide on DNA2) could be brought into close proximity by making the two handles partially complementary, increasing their relative concentration and driving the CuAAC reaction (FIG. 1B). Indeed, we were inspired by a rich literature that exists on DNA-templated synthesis, whereby an oligonucleotide scaffold increases the local concentration between two reactive groups tethered to complementary strands. An aspect to this design is that DNA1 and DNA2 are only partially complementary, with additional single-stranded (ss) DNA regions on each. Addition of fully complementary strands can break the DNA1-$MMP_{pep}$-DNA2 hairpin that results from the second coupling reaction through toehold-mediated strand displacement. For full structures/sequences and details on the synthesis, purification, and characterization of all peptides, modified DNA strands, and peptide-DNA conjugates, see Materials and Methods, below.

We analyzed the proximity-aided formation of the DPD triblock molecule using denaturing polyacrylamide gel electrophoresis (PAGE), FIG. 2. Individually, the DNA1-$MMP_{pep}$-(prA) conjugate and DNA2-azide molecule appear as distinct bands on the gel (lanes 1 and 2). We next mixed these two strands at a 1:1 ratio in room temperature (PBS buffer), and added Cu(I), THPTA as a ligand, and ascorbate for the CuAAC reaction (lane 3). However, by denaturing PAGE only the two individual strands were seen, without any higher molecular weight band indicative of covalent coupling. We surmised that these two strands did not form the desired duplex under these conditions, so we annealed them (95-22° C., over 20 min) to ensure hybridization. In the absence of Cu(I), this sample again gave the two individual strands by denaturing PAGE (lane 4). However, exposing this annealed mixture to the CuAAC coupling conditions yielded a higher molecular weight band corresponding to the DNA1-MMP$_{pep}$-DNA2 triblock molecule (lane 5). We note that in FIG. 2, the cartoons show the expected assembled structure, but upon electrophoresis any such secondary structure will be disrupted. Gratifyingly, the yield of the proximity-aided second bioconjugation appeared to be virtually quantitative, with no significant bands seen for the individual component strands. As a result, this DPD conjugate can be used directly in subsequent steps following removal of excess copper and small molecule ligands by spin filtration with a 3 kDa molecular weight cutoff filter.

As previously mentioned, one of our goals for these DPD triblock molecules is to use them as enzymatically-cleavable latches for a DNA nanostructure, e.g. to close the lid of a DNA origami box or "nano-bot". To probe this effect, we used our DPD triblock to link together two model DNA nanostructures: double crossover ("DX") tiles, defined nanoscale objects 14 nm in length and 4 nm wide. DX tiles are composed of five unique strands—two edge strands, one central strand, and two crossover strands—and we designed two tiles that would have DNA1 and DNA2 as respective crossover strands (see FIG. 3A and Examples for tile design and strand composition). We surmised that upon annealing (95-4° C., over 2 h) the constituent strands for these tiles with the DNA1-MMP$_{pep}$-DNA2 conjugate both tiles would form simultaneously, with the full hybridization of DNA1 and DNA2 into the corresponding tiles breaking the DPD hairpin. Addition of MMP8 to the DX tile dimer should cleave MMP$_{pep}$, and restore the two separate DNA nanostructures.

Figure 3:
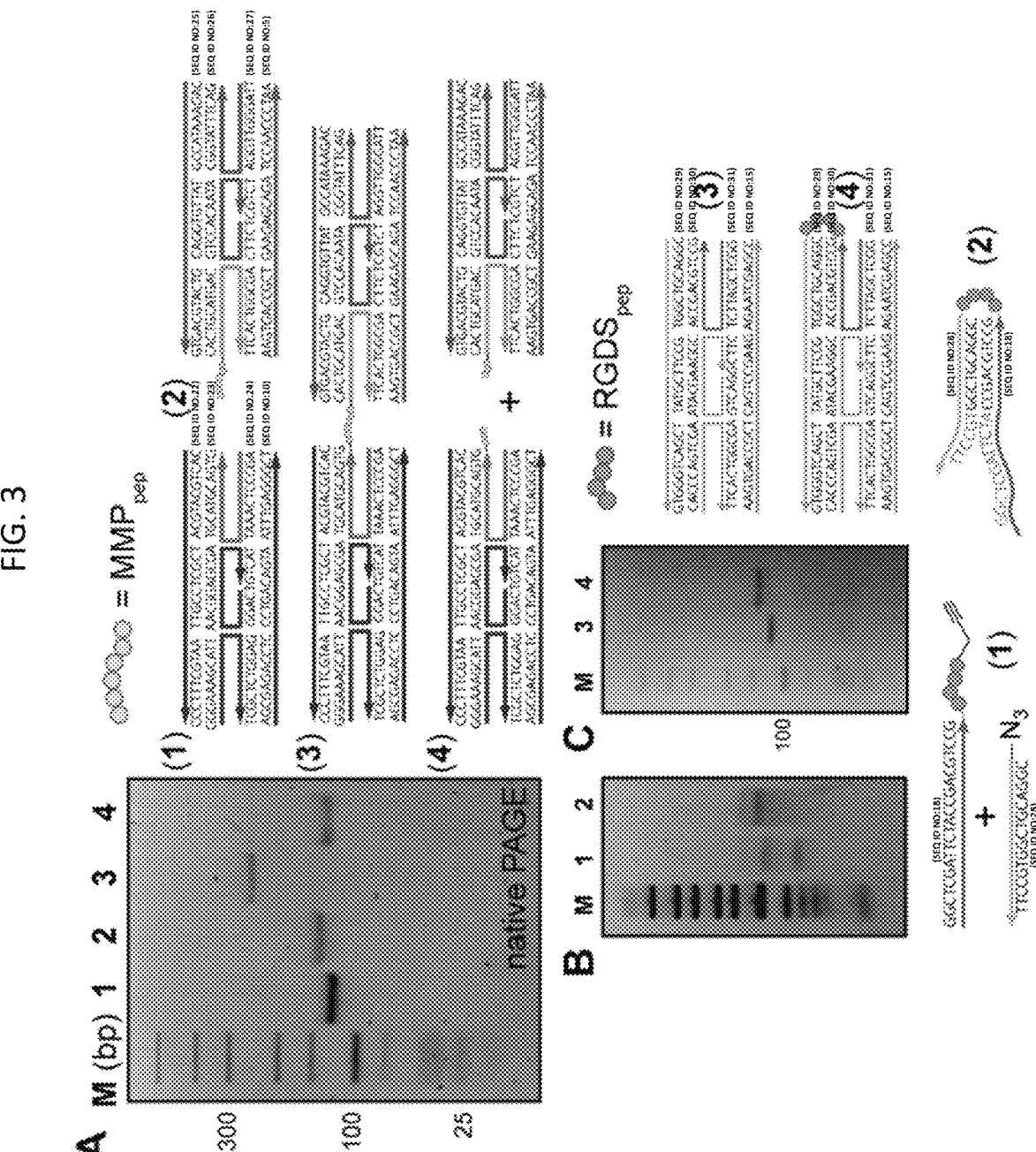
FIG. 3: Nanostructure incorporation of DPD conjugates. Panel A) shows native PAGE of MMP$_{pep}$ incorporated into DX tile nanostructures. Lane M: dsDNA ladder (bp); 1: first DX tile (all DNA); 2: second DX tile, with DNA1-MMP$_{pep}$ incorporated; 3: dimer of DX tiles linked by the DNA1-MMP$_{pep}$-DNA2; 4: DX tile dimer following cleavage of MMP$_{pep}$ by MMP8. Panel B) shows denaturing PAGE analysis of DPD synthesis with RGDS$_{pep}$. Lane M: dsDNA ladder (bp); 1: DNA3-RGDS$_{pep}$+DNA4-azide, annealed, before CuAAC conditions; 2: DNA3-RGDS$_{pep}$+DNA4-azide, annealed, after CuAAC conditions. Panel c) shows incorporation of DNA3-RGDS$_{pep}$-DNA4 into a DX tile. Lane M: dsDNA ladder (bp); 3: DX tile with DNA only; 4: DX tile with RGDS$_{pep}$ DPD. SEQ ID NOs 22, 23, 24, 25, 26, 4, 5, 29, 30, 31, 15, 18, and 28 are shown in FIG. 3.
Figure 4:
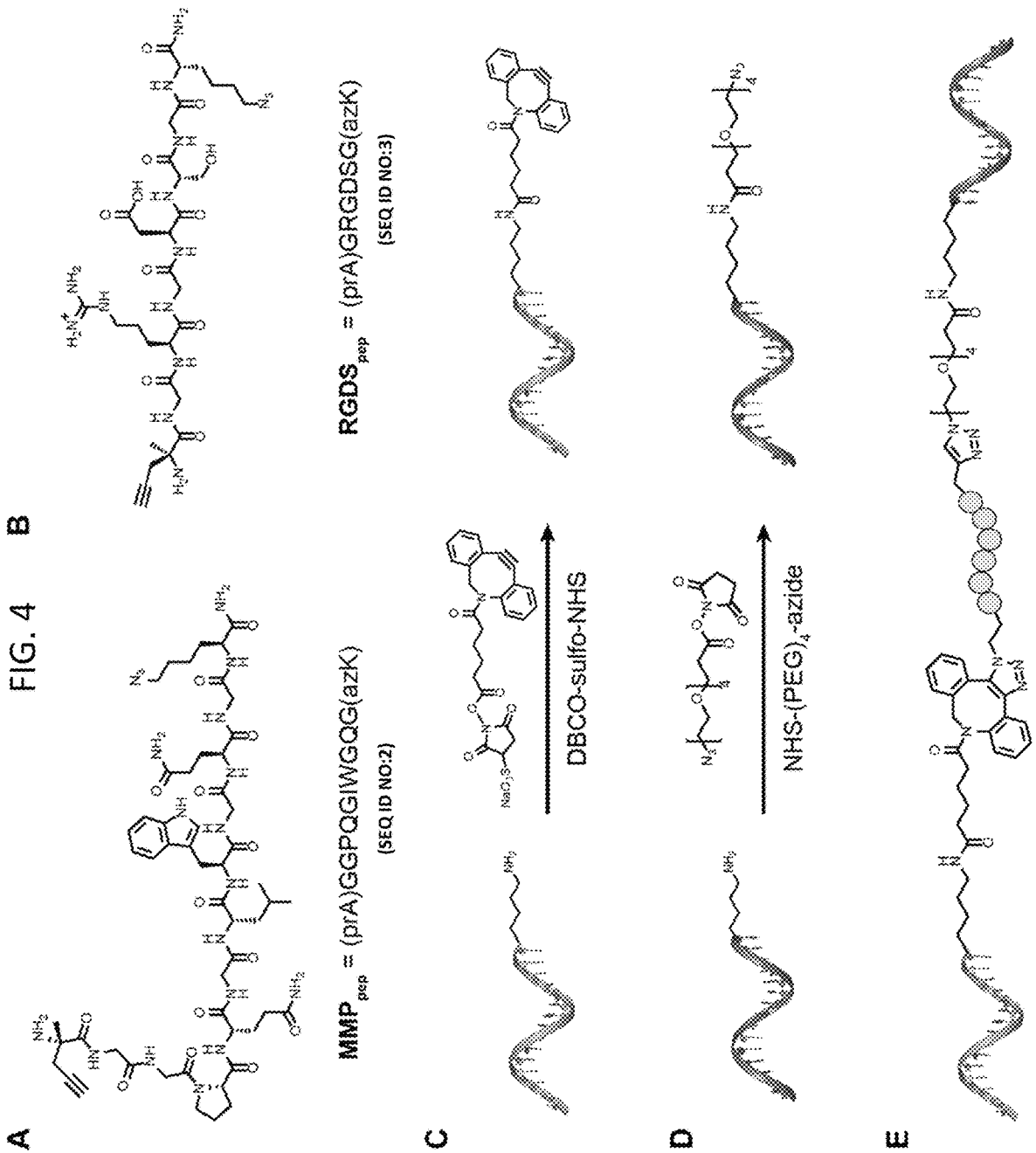
FIG. 4: Panel A) shows the full chemical structures of MMP$_{pep}$ and Panel B) shows the full chemical structure of RGDS$_{pep}$. The noncanonical amino acids propargylalanine (prA) and azidolysine (azK) are indicated. Panels C) and D) show chemical synthesis of DNA-DBCO and DNA-azide, respectively. Panel E) shows the chemical structure of DPD triblock molecule. SEQ ID NO: 2 and 3 are shown in FIG. 4.
Figure 5:
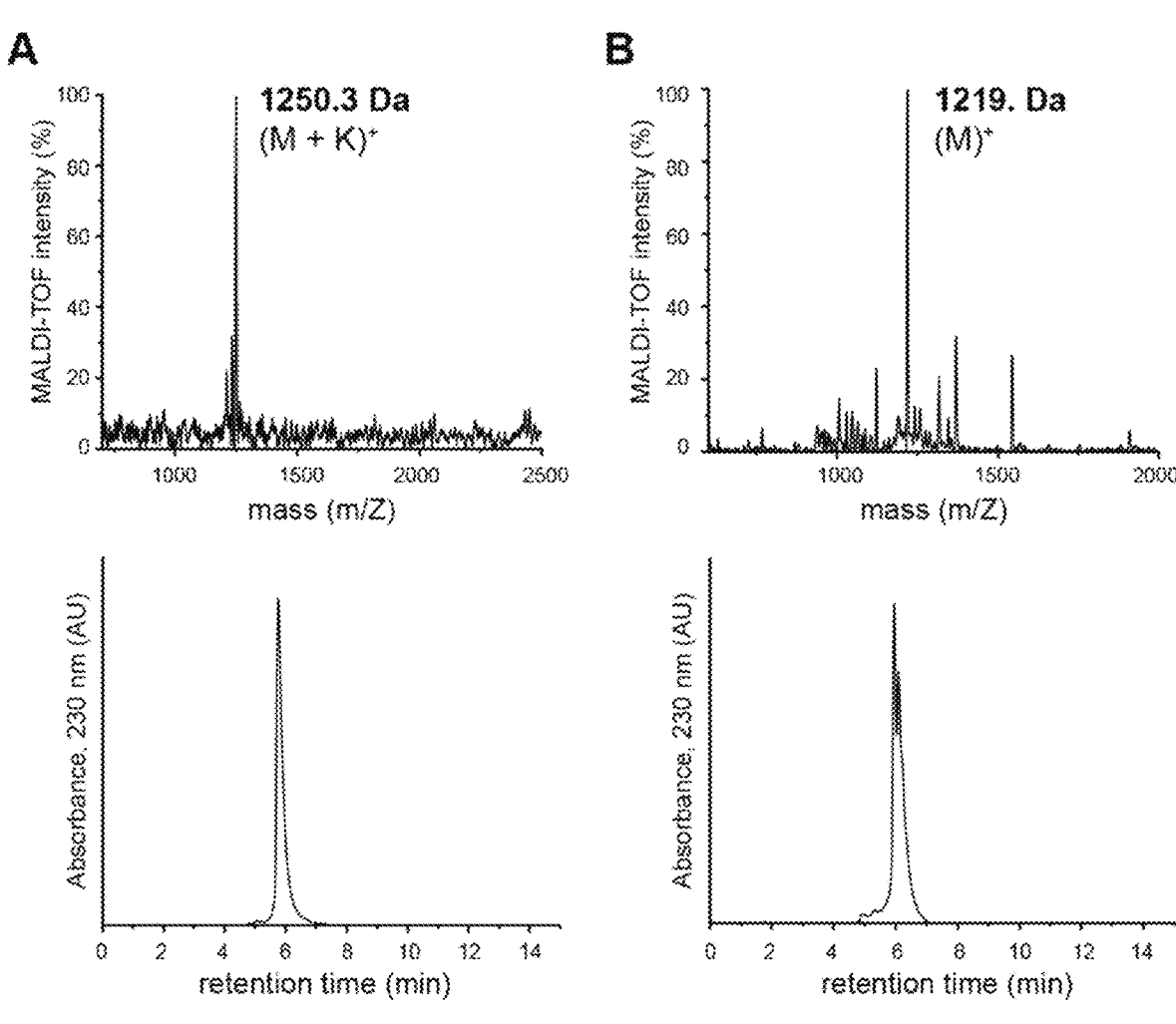
FIG. 5: Characterization confirming the synthesis and purity of MMP$_{pep}$, shown in Panel A) and characterization confirming the synthesis and purity of MMP$_{pep-scram}$ (prA-GQGIPQGWGG (SEQ ID NO:2)-azK) is shown in Panel B). MALDI-TOF mass spectrometry (top) and RP-HPLC (bottom) are presented. The expected mass of both peptides is 1216.6 Da.
Figure 6:
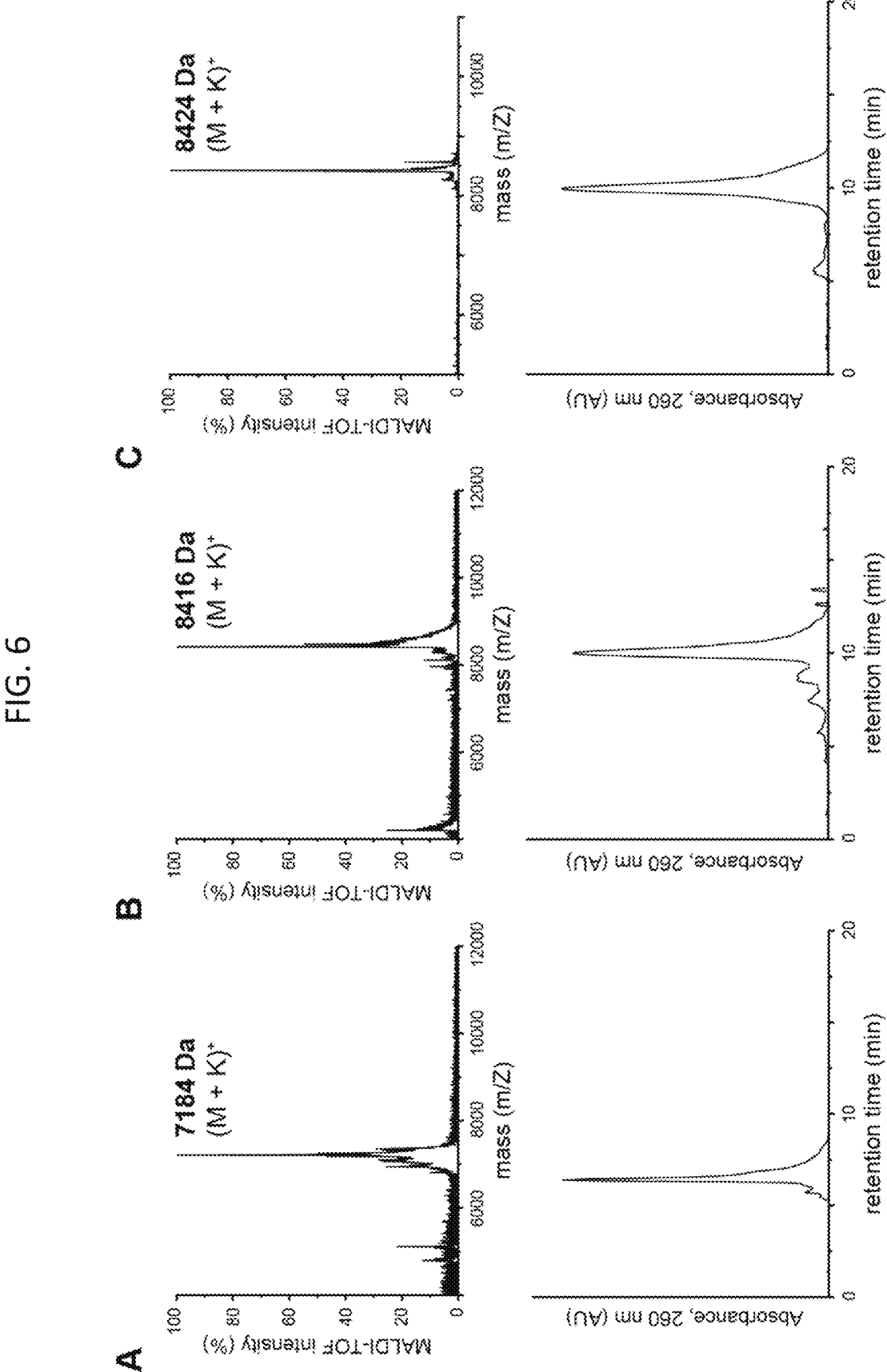
FIG. 6: Characterization confirming the synthesis and purity of DNA2-azide is shown in Panel A), DNA1-MMP$_{pep}$ is shown in panel B), and DNA1-MMP$_{pep-scram}$ is shown in panel C) using MALDI-TOF mass spectrometry (top) and RP-HPLC (bottom). The expected masses are 7148 Da (A) and 8366 Da (B and C).
Figure 9:
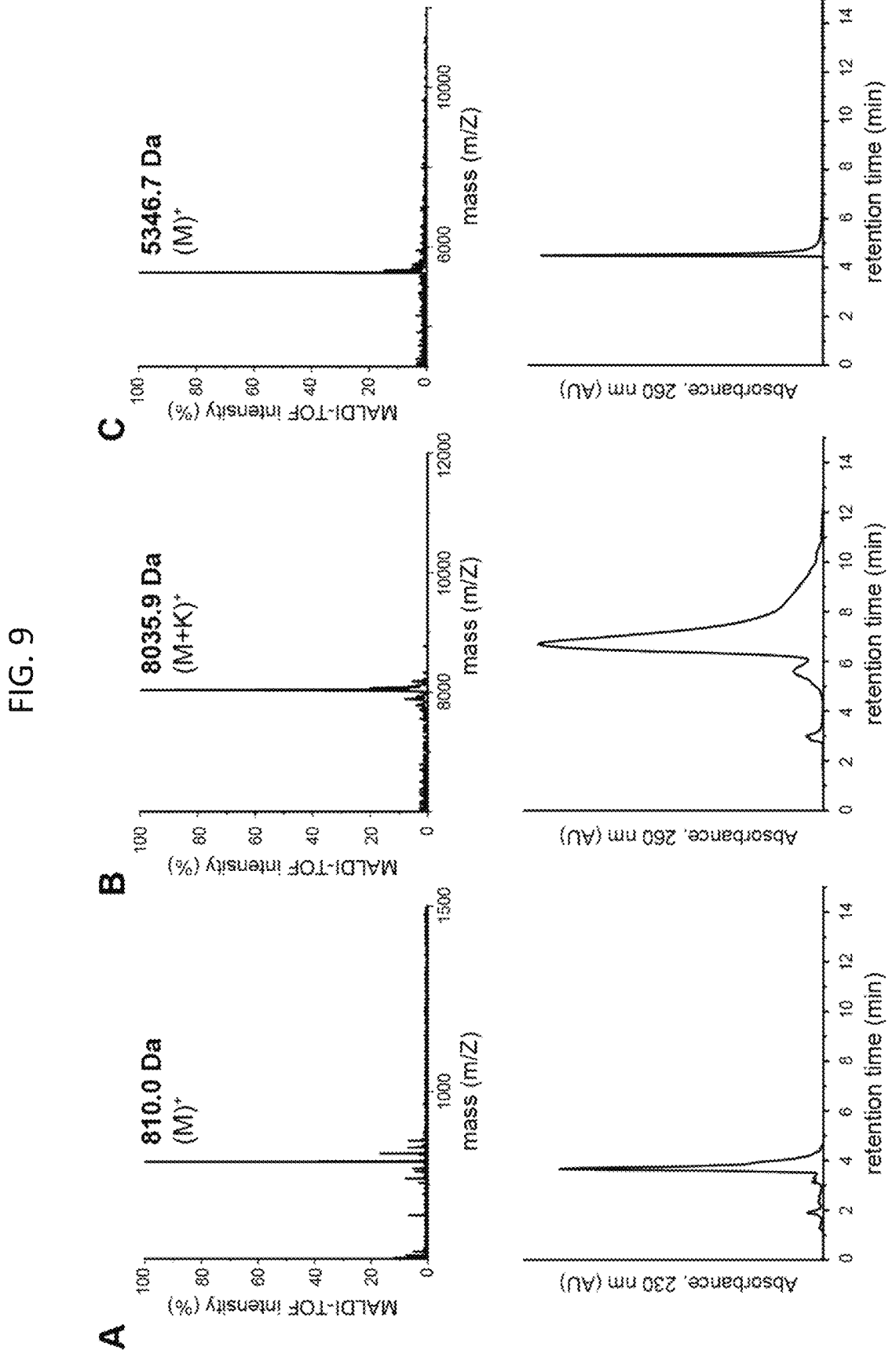
FIG. 9: Characterization confirming the synthesis and purity of (A) RGDS peptide (expected mass 809.39), (B) DNA-RGDS (expected mass 7992), and (C) DNA-azide (expected mass 5346) using MALDI-TOF mass spectrometry and RP-HPLC chromatography.

We probed this system by native (non-denaturing) PAGE, FIG. 3A. Lanes 1 and 2 show the annealed DX tile with DNA2 incorporated, and the second DX tile with DNA1-MMP$_{pep}$-(prA) respectively. Both lanes show a single, clear band corresponding to the desired tiles; the DX tile with DNA1-MMP$_{pep}$-(prA) runs a bit more slowly due to the added mass of the peptide. Lane 3, which contains the product of annealing the tile strands with DNA1-MMP$_{pep}$-DNA2, shows a clear upper band corresponding to the tile dimer, linked by the peptide. Following addition of MMP8 (4 ng protein, incubation for 48 h at 37° C. in PBS) a single band is once again seen, corresponding to the individual tiles; this band has a mobility between those in lanes 1 and 2 because each tile bears only half the peptide after cleavage. We conducted control experiments with a tile dimer linked by a peptide where the residues in MMP$_{pep}$ were randomly scrambled to yield MMP$_{pep-scram}$ (sequence: (prA)GQ-GIPQGWGG(azK); SEQ ID NO:2). This peptide, which should not be responsive to MMP8, did not show any cleavage to individual tiles (FIG. 8). These results are, to our knowledge, the first demonstration of a peptide bearing orthogonal DNA handles being used to link two DNA nanostructures, and its enzymatic responsiveness will find use in protease-responsive nanomaterials or DNA-hybrid biomaterials.

Figure 10:
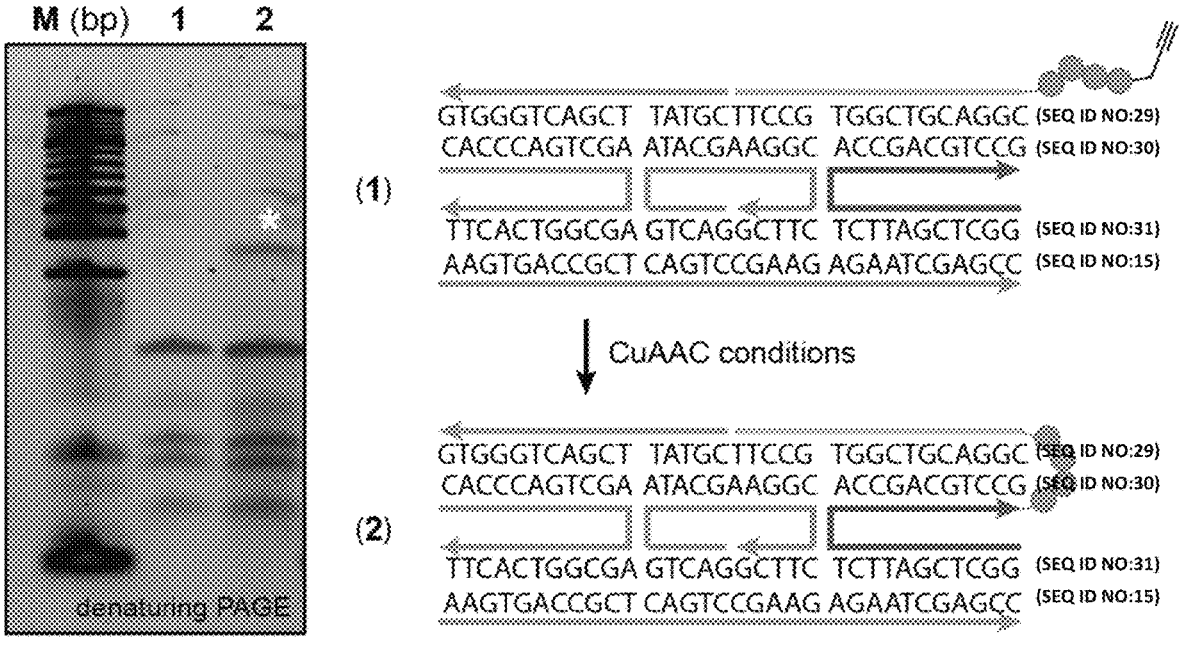
FIG. 10: Synthesis of a DPD triblock on an assembled nanostructure. Denaturing PAGE showing the annealed tile before exposure to CuAAC conditions (1) and after (2). The appearance of an upper band (yellow star) corresponds to the complete DPD conjugate. SEQ ID NOs 29, 30, 31, and 15 are shown in FIG. 10.

Another use for DPD triblock molecules is for constraining peptides into a loop structure through the formation of a hairpin, in order to bias the peptide into a biologically active conformation. Due to our interest in DNA nanostructures as biomaterial scaffolds for peptides, we asked whether the integrin-binding peptide RGDS (derived from fibronectin) could be synthesized as a DPD. Constraining RGDS in a cyclic conformation—which approximates its presentation on fibronectin—has been shown to increase its binding efficiency several orders of magnitude. We thus synthesized RGDS$_{pep}$ (sequence: (prA)GRGDSG(azK); SEQ ID NO:3), and coupled it to DNA3-DBCO via SPAAC; here, DNA3 comprises part of a DX tile edge strand. We then annealed the DNA3-RGDS$_{pep}$-(prA) conjugate with DNA4-azide (where DNA4 is the adjacent crossover strand of the tile), exposed it to CuAAC conditions, and analyzed the reaction by denaturing PAGE (FIG. 3B). As with the MMP$_{pep}$ experiments in FIG. 2, before exposure to the CuAAC conditions the sample denatures back to two individual bands (lane 1), but afterwards primarily a single band is seen at a higher retention corresponding to the DNA3-RGDS$_{pep}$-DNA4 triblock with almost quantitative yield (lane 2). We next took this unpurified sample, and annealed it with the other strands of a DX tile, and analyzed the sample by native PAGE (FIG. 3C). Compared with the DX tile comprised entirely of DNA (lane 3), the DX tile bearing the DPD ran at a slightly higher retention due to the incorporation of the peptide (lane 4). Thus, the RGDS$_{pep}$ DPD could be constrained in a loop conformation on a DNA nanostructure, paving the way for creating bioactive nanomaterials with the shape programmability of DNA nanotechnology. We also explored carrying out the second conjugation reaction directly on the tile, by annealing the DNA3-RGDS$_{pep}$-(prA) conjugate with the other strands of the DX tile (including DNA4-azide) and then exposing the assembled structure to the CuAAC conditions. Analyzing the mixture by denaturing PAGE yielded the individual component strands of the tile, but also a higher band corresponding to the DNA3-RGDS$_{pep}$-DNA4 triblock molecule (FIG. 10). Interestingly, installing the azide at the 5' end of DNA4 (as opposed to the 3' end) gave no reaction, most likely because the reactive ends were slightly too far to facilitate coupling.

Figure 11:
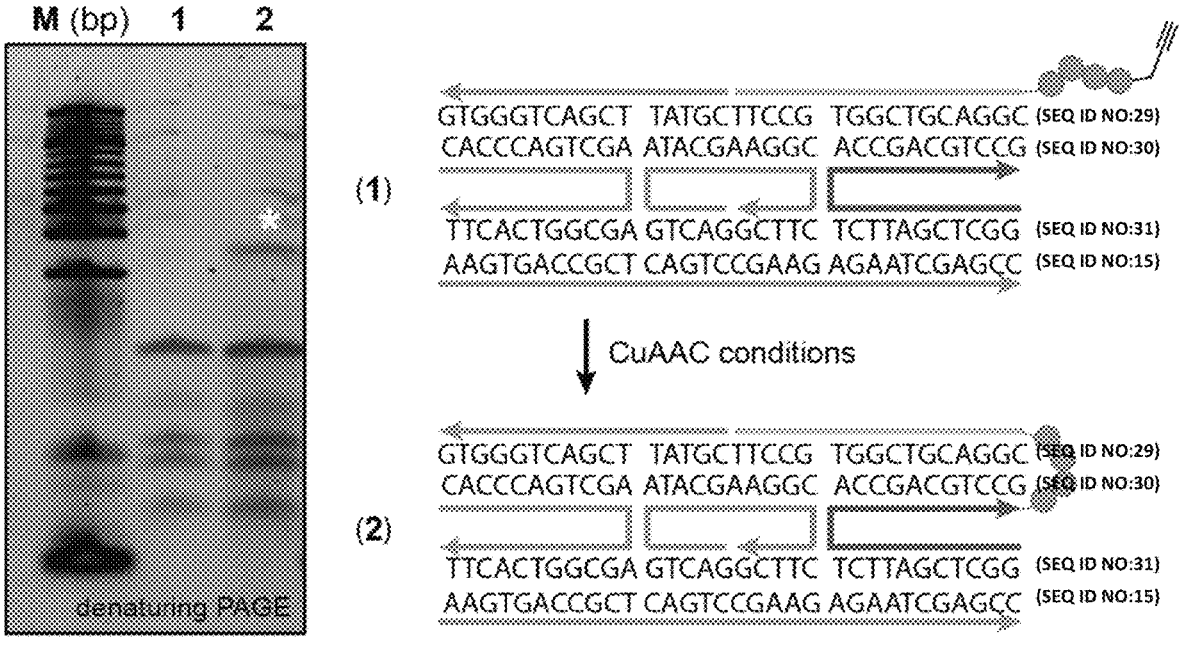
FIG. 11: Proposed route to produce DNA-peptide-DNA-peptide-DNA pentablock molecules (or, in principle, higher order copolymers). Two DPD conjugates can be further linked by splint ligation by incorporating a 5'-phosphate into one of the DNA handles and using DNA ligase.

Taken together, our results show that DPD triblock molecules can be synthesized through sequential SPAAC and CuAAC, using DNA hybridization to drive the second reaction with high efficiency. This method can be used on individual strands, or carried out directly on a pre-formed nanostructure. In addition to enzymatically-responsive peptide latches and single peptide loops, our approach can in principle be extended to alternating (peptide-DNA)N copolymers by concatenating multiple DPD triblock molecules, e.g. via splint ligation (FIG. 11). Thus, it is conceivable that such an alternating copolymer could be "folded" into a well-defined nanostructure (akin to recent reports with single-stranded DNA and RNA origami with multiple peptide loops, for multivalent target binding using avidity effects. Although our approach was demonstrated for peptides, proximity-aided DNA conjugation could in theory be extended to proteins, as recently demonstrated using a different mechanism, paving the way for conformational control of protein display, or synthesis of alternating protein-DNA copolymers in the future.

1. T. MacCulloch, A. Buchberger and N. Stephanopoulos, *Organic & Biomolecular Chemistry*, 2019, 17, 1668-1682.
2. E. M. Zubin, E. A. Romanova, E. M. Volkov, V. N. Tashlitsky, G. A. Korshunova, Z. A. Shabarova and T. S. Oretskaya, *Febs Letters*, 1999, 456, 59-62.
3. M. Gooding, M. Malhotra, J. C. Evans, R. Darcy and C. M. O'Driscoll, *European Journal of Pharmaceutics and Biopharmaceutics*, 2016, 107, 321-340.

4. S. Abes, H. M. Moulton, P. Clair, P. Prevot, D. S. Youngblood, R. P. Wu, P. L. Iversen and B. Lebleu, *Journal of Controlled Release,* 2006, 116, 304-313.

5. J. S. Kang, J. L. Meier and P. B. Dervan, *Journal of the American Chemical Society,* 2014, 136, 3687-3694.

6. R. Juliano, M. R. Alam, V. Dixit and H. Kang, *Nucleic Acids Research,* 2008, 36, 4158-4171.

7. K. Astakhova, R. Ray, M. Taskova, J. Uhd, A. Carstens and K. Morris, *Molecular pharmaceutics,* 2018, 15, 2892-2899.

8. M. Taskova, A. Mantsiou and K. Astakhova, *Chembiochem,* 2017, 18, 1671-1682.

9. R. Freeman, N. Stephanopoulos, Z. Alvarez, J. A. Lewis, S. Sur, C. M. Serrano, J. Boekhoven, S. S. Lee and S. I. Stupp, *Nature Communications,* 2017, 8.

10. R. Freeman, M. Han, Z. Álvarez, J. A. Lewis, J. R. Wester, N. Stephanopoulos, M. T. McClendon, C. Lynsky, J. M. Godbe, H. Sangji, E. Luijten and S. I. Stupp, *Science (American Association for the Advancement of Science),* 2018, 362, 808-813.

11. M. L. Daly, Y. Gao and R. Freeman, *Bioconjugate chemistry,* 2019, 30, 1864-1869.

12. C. Li, A. Faulkner-Jones, A. R. Dun, J. Jin, P. Chen, Y. Z. Xing, Z. Q. Yang, Z. B. Li, W. M. Shu, D. S. Liu and R. R. Duncan, *Angewandte Chemie-International Edition,* 2015, 54, 3957-3961.

13. C. Li, P. Chen, Y. Shao, X. Zhou, Y. Z. Wu, Z. Q. Yang, Z. B. Li, T. Weil and D. S. Liu, *Small,* 2015, 11, 1138-1143.

14. A. Finke, H. Busskamp, M. Manea and A. Marx, *Angewandte Chemie-International Edition,* 2016, 55, 10136-10140.

15. N. Gour, D. Kedracki, I. Safir, K. X. Ngo and C. Vebert-Nardin, *Chemical Communications,* 2012, 48, 5440-5442.

16. M. Kye and Y. B. Lim, *Angewandte Chemie-International Edition,* 2016, 55, 12003-12007.

17. A. Chotera, H. Sadihov, R. Cohen-Luria, P. A. Monnard and G. Ashkenasy, *Chemistry-a European Journal,* 2018, 24, 10128-10135.

18. H. Lee, A. K. R. Lytton-Jean, Y. Chen, K. T. Love, A. I. Park, E. D. Karagiannis, A. Sehgal, W. Querbes, C. S. Zurenko, M. Jayaraman, C. G. Peng, K. Charisse, A. Borodovsky, M. Manoharan, J. S. Donahoe, J. Truelove, M. Nahrendorf, R. Langer and D. G. Anderson, *Nature Nanotechnology,* 2012, 7, 389-393.

19. F. A. Rogers, M. Manoharan, P. Rabinovitch, D. C. Ward and P. M. Glazer, *Nucleic Acids Research,* 2004, 32, 6595-6604.

20. S. Abes, H. Moulton, J. Turner, P. Clair, J. P. Richard, P. Iversen, M. J. Gait and B. Lebleu, *Biochemical Society Transactions,* 2007, 35, 53-55.

21. C. Cordier, F. Boutimah, M. Bourdeloux, F. Dupuy, E. Met, P. Alberti, F. Loll, G. Chassaing, F. Burlina and T. E. Saison-Behmoaras, *Plos One,* 2014, 9.

22. O. A. Patutina, E. V. Bichenkova, S. K. Miroshnichenko, N. L. Mironova, L. T. Trivoluzzi, K. K. Burusco, R. A. Bryce, V. V. Vlassov and M. A. Zenkova, *Biomaterials,* 2017, 122, 163-178.

23. D. Y. Zhang and G. Seelig, *Nature Chemistry,* 2011, 3, 103-113.

24. N. Stephanopoulos, R. Freeman, H. A. North, S. Sur, S. J. Jeong, F. Tantakitti, J. A. Kessler and S. I. Stupp, *Nano Letters,* 2015, 15, 603-609.

25. A. Buchberger, C. R. Simmons, N. E. Fahmi, R. Freeman and N. Stephanopoulos, *Journal of the American Chemical Society,* 2020, 142, 1406-1416.

26. A. Sprengel, P. Lill, P. Stegemann, K. Bravo-Rodriguez, E.-C. Schoneweiß, M. Merdanovic, D. Gudnason, M. Aznauryan, L. Gamrad, S. Barcikowski, E. Sanchez-Garcia, V. Birkedal, C. Gatsogiannis, M. Ehrmann and B. Saccà, *Nature communications,* 2017, 8, 14472-14472.

27. B. A. R. Williams, K. Lund, Y. Liu, H. Yan and J. C. Chaput, *Angewandte Chemie-International Edition,* 2007, 46, 3051-3054.

28. Z. W. Xia, P. Wang, X. W. Liu, T. Liu, Y. N. Yan, J. Yan, J. Zhong, G. Sun and D. N. He, *Biochemistry,* 2016, 55, 1326-1331.

29. E. Spruijt, S. E. Tusk and H. Bayley, *Nature Nanotechnology,* 2018, 13, 739-+.

30. T. Machida, S. Dutt and N. Winssinger, *Angewandte Chemie (International ed.),* 2016, 55, 8595-8598.

31. L. Roglin, M. R. Ahmadian and O. Seitz, *Angewandte Chemie (International ed.),* 2007, 46, 2704-2707.

32. L. Röglin, F. Altenbrunn and O. Seitz, *Chembiochem: a European journal of chemical biology,* 2009, 10, 758-765.

33. S. Thurley, L. Roglin and O. Seitz, *Journal of the American Chemical Society,* 2007, 129, 12693-12695.

34. K. J. Oh, K. J. Cash, A. A. Lubin and K. W. Plaxco, *Chemical communications (Cambridge, England),* 2007, 4869-4871.

35. M. Fischbach, U. Resch-Genger and O. Seitz, *Angewandte Chemie (International ed.),* 2014, 53, 11955-11959.

36. G. Hayashi, M. Yanase, Y. Nakatsuka and A. Okamoto, *Biomacromolecules,* 2019, 20, 1246-1253.

37. S. M. Douglas, I. Bachelet and G. M. Church, *Science,* 2012, 335, 831-834.

38. J. Li, A. Johnson-Buck, Y. R. Yang, W. M. Shih, H. Yan and N. G. Walter, *Nature nanotechnology,* 2018, 13, 723-729.

39. B. A. Badeau, M. P. Comerford, C. K. Arakawa, J. A. Shadish and C. A. Deforest, *Nature chemistry,* 2018, 10, 251-258.

40. Y. Chau, Y. Luo, A. C. Y. Cheung, Y. Nagai, S. G. Zhang, J. B. Kobler, S. M. Zeitels and R. Langer, *Biomaterials,* 2008, 29, 1713-1719.

41. Y. Chau, F. E. Tan and R. Langer, *Bioconjugate Chemistry,* 2004, 15, 931-941.

42. M. Shadidi and M. Sioud, *Drug Resistance Updates,* 2003, 6, 363-371.

43. A. Gutierrez-Fernandez, A. Fueyo, A. R. Folgueras, C. Garabaya, C. J. Pennington, S. Pilgrim, D. R. Edwards, D. L. Holliday, J. L. Jones, P. N. Span, C. G. J. Sweep, X. S. Puente and C. Lopez-Otin, *Cancer research (Chicago, Ill.),* 2008, 68, 2755-2763.

44. R. K. Bruick, P. E. Dawson, S. B. Kent, N. Usman and G. F. Joyce, *Chemistry & Biology,* 1996, 3, 49-56.

45. A. Erben, T. N. Grossmann and O. Seitz, *Angewandte Chemie International Edition,* 2011, 50, 2828-2832.

46. J. Niu, R. Hili and D. R. Liu, *Nature Chemistry,* 2013, 5, 282-292.

47. C. Guo, C. P. Watkins and R. Hili, *Journal of the American Chemical Society,* 2015, 137, 11191-11196.

48. S. Middel, C. H. Panse, S. Nawratil and U. Diederichsen, *Chembiochem,* 2017, 18, 2328-2332.

49. N. C. Seeman, *Annual Review of Biophysics and Biomolecular Structure,* 1998, 27, 225-248.

50. E. Winfree, F. R. Liu, L. A. Wenzler and N. C. Seeman, *Nature,* 1998, 394, 539-544.

51. P. Sa-Ardyen, A. V. Vologodskii and N. C. Seeman, *Biophysical Journal,* 2003, 84, 3829-3837.

52. X. J. Li, X. P. Yang, J. Qi and N. C. Seeman, *Journal of the American Chemical Society*, 1996, 118, 6131-6140.

53. T. J. Fu and N. C. Seeman, *Biochemistry*, 1993, 32, 3211-3220.

54. P. S. Ghosh and A. D. Hamilton, *Journal of the American Chemical Society*, 2012, 134, 13208-13211.

55. M. Marczynke, K. Gröger and O. Seitz, *Bioconjugate chemistry*, 2017, 28, 2384-2392.

56. F. Diezmann, L. Von Kleist, V. Haucke and O. Seitz, *Organic & biomolecular chemistry*, 2015, 13, 8008-8015.

57. H. Eberhard, F. Diezmann and O. Seitz, *Angewandte Chemie-International Edition*, 2011, 50, 4146-4150.

58. A. Buchberger, H. Saini, K. R. Eliato, A. Zare, R. Merkley, Y. Xu, J. Bernal, R. Ros, M. Nikkhah and N. Stephanopoulos, *Chembiochem: a European journal of chemical biology*, 2021, 22, 1755-1760.

59. T. G. Kapp, F. Rechenmacher, S. Neubauer, O. V. Maltsev, E. A. Cavalcanti-Adam, R. Zarka, U. Reuning, J. Notni, H.-J. Wester, C. Mas-Moruno, J. Spatz, B. Geiger and H. Kessler, *Scientific reports*, 2017, 7, 39805-39805.

60. J. F. Van Agthoven, J.-P. Xiong, J. L. Alonso, X. Rui, B. D. Adair, S. L. Goodman and M. A. Arnaout, *Nature structural & molecular biology*, 2014, 21, 383-388.

61. P. R. Patel, R. C. Kiser, Y. Y. Lu, E. Fong, W. C. Ho, D. A. Tirrell and R. H. Grubbs, *Biomacromolecules*, 2012, 13, 2546-2553.

62. A. Krammer, D. Craig, W. E. Thomas, K. Schulten and V. Vogel, *Matrix biology*, 2002, 21, 139-147.

63. N. Assa-Munt, X. Jia, P. Laakkonen and E. Ruoslahti, *Biochemistry (Easton)*, 2001, 40, 2373-2378.

64. D. J. Leahy, I. Aukhil and H. P. Erickson, *Cell (Cambridge)*, 1996, 84, 155-164.

65. M. Aumailley, M. Gurrath, G. Müller, J. Calvete, R. Timpl and H. Kessler, *FEBS letters*, 1991, 291, 50-54.

66. N. Assa-Munt, X. Jia, P. Laakkonen and E. Ruoslahti, *Biochemistry*, 2001, 40, 2373-2378.

67. J. Samanen, F. Ali, T. Romoff, R. Calvo, E. Sorenson, J. Vasko, B. Storer, D. Berry, D. Bennett, M. Strohsacker, D. Powers, J. Stadel and A. Nichols, *Journal of medicinal chemistry*, 1991, 34, 3114-3125.

68. C. J. White and A. K. Yudin, *Nature chemistry*, 2011, 3, 509-524.

69. M. Pfaff, K. Tangemann, B. Müller, M. Gurrath, G. Müller, H. Kessler, R. Timpl and J. Engel, *The Journal of biological chemistry*, 1994, 269, 20233-20238.

70. D. Han, X. Qi, C. Myhrvold, B. Wang, M. Dai, S. Jiang, M. Bates, Y. Liu, B. An, F. Zhang, H. Yan and P. Yin, *Science (American Association for the Advancement of Science)*, 2017, 358, eaao2648.

71. C. B. Rosen, A. L. B. Kodal, J. S. Nielsen, D. H. Schaffert, C. Scavenius, A. H. Okholm, N. V. Voigt, J. J. Enghild, J. Kjems, T. Tørring and K. V. Gothelf, *Nature chemistry*, 2014, 6, 804-809.

72. A. Buchberger, C. R. Simmons, N. E. Fahmi, R. Freeman, N. Stephanopoulos*, "Hierarchical assembly of nucleic acid/coiled-coil peptide nanostructures" *J. Am. Chem. Soc.* 2020, 142, 1406-1416.

Materials and Methods

Peptide Synthesis. All peptides were synthesized on a CEM Liberty Blue microwave-assisted synthesizer at a 0.1 mmol scale, using a Rink amide resin and standard Fmoc chemistry according to previously reported protocols. Briefly, a 20% piperidine solution was used for deprotection, 0.5 M diisopropylcarbodiimide was used as an activator, and a solution of 1 M oxyma with 0.1 M diisopropylethylamine was used as an activator base. Amino acids were added to the resin at a concentration of 0.2 M and coupled for 4 min. The peptide was cleaved from the resin at room temperature for 4 h using a 95:2.5:2.5 mixture of trifluoroacetic acid (TFA): triisopropyl silane (TIPS):water. The crude peptide was precipitated into cold diethyl ether, and resuspended in water+0.1 M TFA. Peptides were purified on a Waters HPLC instrument using a gradient of 0-80% acetonitrile with 0.1% TFA. Fractions with an absorbance (230 nm) reaching a threshold of 300 mAU were collected and analyzed using matrix assisted laser desorption ionization time-of-flight (MALDI-TOF) mass spectrometry (MS). All pure fractions with the corresponding peptide mass were pooled and lyophilized.

DNA purification. All oligonucleotides used were purchased from Integrated DNA technologies (Coralville, Iowa) and purified using a 14% urea-based denaturing polyacrylamide gel electrophoresis (PAGE). The gel was run in 1× Tris, boric acid, EDTA running buffer at 45 volts for 2 h. The desired band was detected using UV shadowing, excised, and eluted using a buffer of ammonium acetate, magnesium acetate, and EDTA. The DNA was precipitated using 100% ethanol followed by centrifugation at 16,000 RPM for 5 min. The pellet was resuspended in Nanopure water and the concentration was obtained from the 260 nm absorbance using a Nanodrop instrument.

Synthesis of peptide-DNA conjugates using SPAAC. Amine modified oligonucleotides were dissolved in 1×PBS (pH 7.5) buffer to a concentration of 1 μM. To the oligonucleotide solution was 5 equivalents of NHS-Sulfo-DBCO ester (as a solution in DMSO). The mixture was incubated at RT for 4 h, after which a second aliquot (5 equivalents) of the NHS-sulfo-DBCO was added and the mixture was incubated at RT overnight. The DBCO-modified DNA was purified from unreacted DNA using reverse phase HPLC on an Agilent 1220 instrument, using a Zorbax Eclipse C18 column with 50 mM triethylammonium acetate and methanol as the running buffers. A gradient of 0-70% methanol was applied over 45 min while monitoring the absorbance at both 260 and 309 nm, the peak absorbance wavelengths of the DNA and the DBCO, respectively. The peak displaying an absorbance at both wavelengths was collected and exchanged into water using a 3 kDa molecular weight cut off (MWCO) filter. The DBCO-modified DNA was then mixed with the azidolysine containing peptide in a 1:4 ratio (DNA: peptide) in 1×PBS (pH 7.5) buffer, and incubated at RT overnight. The DNA-peptide conjugate was purified away from the DNA-DBCO using the same HPLC method as for the DNA-DBCO conjugate. All fractions were characterized by MALDI-TOF MS to identify the desired peak.

Synthesis of a DNA-peptide-DNA triblock via proximity-aided CuAAC.

Amine-modified DNA was reacted with NHS-PEG$_4$-azide (Click Chemistry Tools) and purified using the same method as for DBCO-DNA. Fractions containing the azide-DNA were identified using MALDI-TOF MS. The peptide oligonucleotide conjugate, obtained following SPAAC conjugation, and the azide modified DNA strand were mixed in a 1:1 stoichiometry in 2×PBS (pH 7.5) at a concentration of 15 μM and annealed using a thermal gradient of 95-4° C. over 1 h. Cu(I)-catalyzed click was used to conjugate the DNA-peptide (containing propargylalanine) to the azide modified DNA according to the following procedure: a mixture was made containing (final concentrations) 10 μM of the annealed DNA mixture, 1 mM aminoguanidine, 10 μM of a 1:5 mixture of copper [CuSO$_4$]: tris-hydroxypropyltriazolylmethylamine ligand (THPTA), and 20 mM PBS. 100 mM sodium ascorbate was added to the mixture and the reaction was carried out for 3 h at RT, after which point it was quenched with 250 mM EDTA.

Cleavage of peptide using MMP. DNA nanostructures linked by the MMP cleavable peptide were incubated in with 10 ng of human matrix metalloproteinase 8 (PerkinElmer) for 48 h in 1×PBS buffer (pH 7.4).

MALDI-TOF MS Characterization. All samples were characterized using a Bruker Microflex LRF MALDI. Peptides were analyzed in positive reflector mode using α-cyanohydroxycinnaminic acid as a matrix. DNA and DNA-peptide conjugates analyzed shot using positive linear mode with either hydroxypicolinic acid or 6-aza-2-thiothymine with 10 mM ammonium citrate.

Polyacrylamide gel electrophoresis (PAGE). DPD conjugates were probed via urea-based denaturing polyacrylamide gel (8%) electrophoresis at 45 V for 90 min. DX tiles were analyzed using 6% native polyacrylamide gels, with 1×TAE containing 12.5 mM $Mg^{2+}$ as a running buffer, at 200 V for 160 min.

DNA Sequences

TABLE 1

Sequences of the DNA oligonucleotides used to synthesize the DNA-peptide-DNA conjugates, as well as the strands that comprise the DX tiles. "$NH_2$" denotes an amine linked by a C6 alkyl linker.

MMP DX Tile 1

| | |
|---|---|
| Top | CAGAAATACCGTATTGTGGACGTCATGCAGTG (SEQ ID NO: 4) |
| Bottom | AAGTGACCGCTGAAGAGCAGATCCAACCCTAA (SEQ ID NO: 5) |

TABLE 1-continued

Sequences of the DNA oligonucleotides used to synthesize the DNA-peptide-DNA conjugates, as well as the strands that comprise the DX tiles. "$NH_2$" denotes an amine linked by a C6 alkyl linker.

| | |
|---|---|
| Center | TCTTCGTCCACAATATCTGC (SEQ ID NO: 6) |
| DNA1 | $NH_2$-CACTGCATGACAGCGGTCACTT (SEQ ID NO: 7) |
| Right | TTAGGGTTGGACGGTATTTCAG (SEQ ID NO: 8) |

MMP DX Tile 2

| | |
|---|---|
| Top | CACTGCATGCATCGCTCCGTTAATGCTTTCCC (SEQ ID NO: 9) |
| Bottom | AGCGAGACCTCCCTGACAGTAATTTGAGGGCT (SEQ ID NO: 10) |
| Center | TCAGGAACGGAGCGATACTG (SEQ ID NO: 11) |
| Left | GGGAAAGCATTGAGGTCTCGCT (SEQ ID NO: 12) |
| DNA2 | AGCCCTCAAATTGCATGCAGTG-$NH_2$ (SEQ ID NO: 13) |

RGDS DX Tile

| | |
|---|---|
| Top | CGTATTCGACTGGGTG (SEQ ID NO: 14) |
| Bottom | AAGTGACCGCTCAGTCCGAAGAGAATCGAGCC (SEQ ID NO: 15) |
| Center | GACTGATACGAAGGCCTTCG (SEQ ID NO: 16) |
| Left | CACCCAGTCGAAGCGGTCACTT (SEQ ID NO: 17) |
| DNA3 | GGCTCGATTCTACCGACGTCCG-$NH_2$ (SEQ ID NO: 18) |
| DNA4 | $NH_2$-CGGACGTCGGTGCCTT (SEQ ID NO: 19) |

---

What is claimed:

1. A method for synthesizing a nucleic acid-peptide-nucleic acid conjugate molecule, comprising:

covalently linking a peptide, the peptide comprising a terminal azide group and a terminal alkyne group, with a first nucleic acid strand, the first nucleic acid strand comprising an alkyne functional group, via a first reaction, the first reaction comprising an azide-alkyne cycloaddition, to provide a nucleic acid-peptide conjugate;

hybridizing the first nucleic acid strand of the nucleic acid-peptide conjugate with a second nucleic acid strand, the second nucleic acid strand comprising an azide group, to bring the second nucleic acid strand in proximity to the peptide; and covalently linking the peptide with the second nucleic acid strand via a second reaction, the second reaction comprising an azide-alkyne cycloaddition, to provide the nucleic acid-peptide-nucleic acid conjugate molecule, wherein the first nucleic acid strand and the second nucleic acid strand are partially complementary.

2. The method of claim 1, wherein the first nucleic acid strand and the second nucleic acid strand have different nucleic acid sequences and are not fully complementary.

3. The method of claim 1, wherein the first reaction and the second reaction are orthogonal azide-alkyne cycloaddition reactions.

4. The method of claim 1, wherein the first reaction is a strain-promoted azide-alkyne cycloaddition (SPAAC) reaction, and the second reaction is a copper (I)-catalyzed azide-alkyne cycloaddition (CuAAC) reaction.

5. The method of claim 4, wherein the peptide is modified with an N-terminal or C-terminal azide group, wherein the first nucleic acid strand is modified with a dibenzocyclooctyne group, and wherein the azide group of the peptide reacts with the dibenzocyclooctyne group of the first nucleic acid strand via the SPAAC reaction.

6. The method of claim 5, wherein the peptide is modified with an N-terminal or C-terminal alkyne group, wherein the second nucleic acid strand is modified with an azide group, and wherein the alkyne group of the peptide reacts with the azide group of the second nucleic acid strand via the CuAAC reaction.

7. The method of claim 1, wherein the first nucleic acid strand and the second nucleic acid strand are partially hybridized in the nucleic acid-peptide-nucleic acid conjugate molecule.

8. The method of claim 7, wherein the nucleic acid-peptide-nucleic acid conjugate molecule includes single-stranded overhangs where the first nucleic acid strand and the second nucleic acid strand are unhybridized.

9. The method of claim 7, wherein the nucleic acid-peptide-nucleic acid conjugate molecule is constrained to a hairpin structure by the partial hybridization between the first nucleic acid strand and the second nucleic acid strand.

10. The method of claim 9, further comprising displacing the first nucleic acid strand from the second nucleic acid strand using one or more single-stranded nucleic acid strands that are fully complementary to the first nucleic acid strand and/or the second nucleic acid strand.

11. The method of claim 10, wherein displacing the first nucleic acid strand from the second nucleic acid strand disrupts the hairpin structure of the nucleic acid-peptide-nucleic acid conjugate molecule.

12. The method of claim 1, wherein the peptide is a substrate for enzymatic cleavage, and optionally cleaving the peptide with an enzyme.

13. The method of claim 1, wherein the terminal azide group of the peptide comprises N-terminal azidolysine (azK);

the terminal alkyne group of the peptide comprises C-terminal propargylalanine (prA);

the alkyne group of the first nucleic acid strand comprises dibenzocyclooctyne;

the first reaction comprises strain-promoted azide-alkyne cycloaddition (SPAAC); and the second reaction comprises copper (I)-catalyzed azide-alkyne cycloaddition (CuAAC).

* * * * *